US012788545B2

(12) United States Patent
Zegarelli et al.

(10) Patent No.: US 12,788,545 B2
(45) Date of Patent: Nov. 10, 2026

(54) ORAL APPLIANCE HAVING MEDICAMENT AND METHODS OF MAKING

(71) Applicant: Emanate Biomedical, Inc., New York, NY (US)

(72) Inventors: Peter John Zegarelli, Sleepy Hollow, NY (US); Jarret Scott Fass, New York, NY (US)

(73) Assignee: Emanate Biomedical, Inc., Larchmont, NY (US)

( * ) Notice: Subject to any disclaimer, the term of this patent is extended or adjusted under 35 U.S.C. 154(b) by 46 days.

(21) Appl. No.: 17/622,632

(22) PCT Filed: Nov. 20, 2020

(86) PCT No.: PCT/US2020/061511
§ 371 (c)(1),
(2) Date: Dec. 23, 2021

(87) PCT Pub. No.: WO2021/102265
PCT Pub. Date: May 27, 2021

(65) Prior Publication Data

US 2023/0270533 A1 Aug. 31, 2023

Related U.S. Application Data

(60) Provisional application No. 62/939,132, filed on Nov. 22, 2019.

(51) Int. Cl.
*A61C 19/06* (2006.01)
*G16H 20/13* (2018.01)
(Continued)

(52) U.S. Cl.
CPC .......... *A61C 19/063* (2013.01); *G16H 20/13* (2018.01); *A61C 7/08* (2013.01); *A61C 13/0013* (2013.01);
(Continued)

(58) Field of Classification Search
CPC .............. A61C 19/063; A61C 13/0013; A61C 13/0019; A61C 7/08; A61L 27/54; A61L 2420/00; G16H 20/13
(Continued)

(56) References Cited

U.S. PATENT DOCUMENTS 5,194,003 A 3/1993 Garay
5,460,527 A * 10/1995 Kittelsen .............. A63B 71/085
128/862

(Continued)

FOREIGN PATENT DOCUMENTS

WO 2017/182425 10/2017

OTHER PUBLICATIONS

International Search Report and Written Opinion of the International Searching Authority mailed on Feb. 24, 2021 in International PCT Application No. PCT/US2020/061511 filed Nov. 20, 2020.

(Continued)

*Primary Examiner* — Brian K Talbot
(74) *Attorney, Agent, or Firm* — Sorell, Lenna & Schmidt, LLP

(57) ABSTRACT

An oral appliance and a method of making the oral appliance for delivering a medicament to an oral cavity are provided. The method comprises providing an oral appliance having an exterior and an interior, the interior of the oral appliance configured to contour at least a portion of teeth and/or soft tissue areas of the oral cavity. A robotic dispensing device is provided, the robotic device having an outlet configured to dispense medicament at discrete regions of the interior, the exterior or both the interior and the exterior of the oral appliance; and dispensing the medicament from the outlet of the robotic dispensing device to discrete regions of the
(Continued)

interior, the exterior or both the interior and the exterior of the oral appliance for delivering the medicament to the oral cavity.

10 Claims, 12 Drawing Sheets

(51) Int. Cl.
*A61C 7/08* (2006.01)
*A61C 13/00* (2006.01)
*A61L 27/54* (2006.01)

(52) U.S. Cl.
CPC ........... *A61C 13/0019* (2013.01); *A61L 27/54* (2013.01); *A61L 2420/00* (2013.01)

(58) Field of Classification Search
USPC .......................................................... 427/2.29
See application file for complete search history.

(56) References Cited

U.S. PATENT DOCUMENTS

| | | | | |
|---|---|---|---|---|
| 7,878,801 | B2 | 2/2011 | Abolfathi et al. | |
| 8,075,309 | B2 | 12/2011 | Li et al. | |
| 8,113,837 | B2 | 2/2012 | Zegarelli | |
| 9,089,388 | B2 | 7/2015 | Zegarelli | |
| 10,300,597 | B2 * | 5/2019 | Takahashi | B25J 5/007 |
| 10,993,881 | B1 * | 5/2021 | Karpman | A61J 7/0481 |
| 11,458,002 | B2 * | 10/2022 | Buckley | A61C 19/063 |
| 2002/0110780 | A1 | 8/2002 | Zegarelli | |
| 2006/0084026 | A1 * | 4/2006 | Cinader | A61C 7/146 433/215 |
| 2007/0122362 | A1 | 5/2007 | Giniger et al. | |
| 2008/0015322 | A1 | 1/2008 | Kindt et al. | |
| 2008/0096162 | A1 | 4/2008 | Bardach et al. | |
| 2008/0243306 | A1 * | 10/2008 | Koike | B25J 9/1676 700/250 |
| 2009/0017410 | A1 * | 1/2009 | Raby | A61C 7/146 433/2 |
| 2009/0136893 | A1 * | 5/2009 | Zegarelli | A61C 19/066 433/80 |
| 2010/0285419 | A1 * | 11/2010 | Cinader, Jr. | A61C 7/146 264/19 |
| 2012/0225402 | A1 * | 9/2012 | Crivello | A61K 6/00 523/105 |
| 2013/0331989 | A1 * | 12/2013 | Umeno | G06N 3/008 700/258 |
| 2014/0011162 | A1 | 1/2014 | Zegarelli | |
| 2014/0316564 | A1 * | 10/2014 | Nakamura | G05B 19/19 901/1 |
| 2015/0057675 | A1 | 2/2015 | Akeel et al. | |
| 2015/0306007 | A1 | 10/2015 | Golas et al. | |
| 2016/0008097 | A1 | 1/2016 | Chen et al. | |
| 2016/0256240 | A1 | 9/2016 | Shivapuja et al. | |
| 2016/0256242 | A1 * | 9/2016 | Cinader, Jr. | A61C 19/02 |
| 2016/0256997 | A1 * | 9/2016 | Takahashi | B25J 9/0087 |
| 2016/0278900 | A1 * | 9/2016 | Zegarelli | A61K 35/38 |
| 2016/0278903 | A1 | 9/2016 | Zegarelli | |
| 2017/0007361 | A1 | 1/2017 | Boronkay et al. | |
| 2017/0043896 | A1 * | 2/2017 | Fernandez | A61J 7/0053 |
| 2017/0321316 | A1 * | 11/2017 | Barron | C23C 4/12 |
| 2017/0347956 | A1 * | 12/2017 | Zegarelli | A61B 5/01 |
| 2019/0175495 | A1 | 6/2019 | Taylor et al. | |
| 2019/0247173 | A1 * | 8/2019 | Zegarelli | A61C 19/066 |
| 2019/0247174 | A1 * | 8/2019 | Zegarelli | A61C 9/0046 |
| 2021/0085436 | A1 * | 3/2021 | Evans | A61C 17/228 |
| 2022/0087800 | A1 * | 3/2022 | Wolgin | A61C 19/063 |
| 2022/0117849 | A1 * | 4/2022 | Patil-Graziano | A61C 19/063 |

OTHER PUBLICATIONS

Liang, et al. 3D Printing of a wearble personalized oral delivery device: A first in-human study. Sciencemag.org. May 9, 2018. Retrieved from Internet on Jan. 25, 2021 at https://advances.sciencemag.org/content/4/5/eaat2544.

* cited by examiner

ORAL APPLIANCE HAVING MEDICAMENT AND METHODS OF MAKING

BACKGROUND

Although advances have been made in recent years for the treatment of specific dental diseases, the actual delivery of dental treatment remains a manually intensive process. Oral appliances that allow drug delivery to the oral cavity have been developed that can deliver medicaments via to the oral cavity, for example, through gums, buccal and sublingual areas. These oral appliances are available in universal sizes to generically fit adults or are custom made for a precise fit to the teeth and gums of the individual patient.

Oral appliances that are provided in universal sizes often do not adequately match the patient's actual oral cavity characteristics. This can lead to poor contact in areas where such oral appliances are adapted to deliver the drug. Custom made oral appliances present a better fit to the patient's oral cavity since they are fabricated to match the actual oral cavity in which they are employed.

There are many challenges associated with manufacturing of customized or individualized medicament containing oral appliances that can handle a wide variety of anatomies of the oral cavity. In some instances, oral appliances containing medicament bearing material may not have such material anatomically placed within the oral appliance such that the medicament does not adequately reach the areas it was meant to treat. In other instances, the healthcare provider and/or the patient may not load the medicament accurately within the medicament bearing material.

Robotic systems are employed in a number of different contexts and may be called upon to perform a wide variety of different tasks. Robots typically manipulate objects around them using robotic manipulators such as individual actuators, grippers, or end effectors.

To date robotic systems have not been appreciated to dispense medicament at discrete regions of a custom-made oral appliance. Accordingly, there is a need for a methodology for automating manufacturing of oral appliances for dental treatment. This methodology includes providing oral appliances that can be easily and precisely loaded with medicament at the discrete regions to control delivery of a medicament at the target tissue site within the oral cavity.

SUMMARY

The current application provides a method for automating manufacturing of oral appliances for dental treatment, including providing oral appliances that can be easily and precisely loaded with medicament at the discrete regions to control delivery of a medicament at the target tissue site within the oral cavity.

The method comprises providing an oral appliance having an exterior and an interior, the interior of the oral appliance configured to contour at least a portion of teeth and/or soft tissue areas of the oral cavity. A robotic dispensing device is provided, the robotic device having an outlet configured to dispense medicament at discrete regions of the interior, the exterior or both the interior and the exterior of the oral appliance; and dispensing the medicament from the outlet of the robotic dispensing device to discrete regions of the interior, the exterior or both the interior and the exterior of the oral appliance for delivering the medicament to the oral cavity.

In various aspects, a system for dispensing a medicament into or onto an oral appliance is provided. The system comprises a robotic dispensing device having an outlet configured to dispense medicament at discrete regions of an interior, an exterior or both the interior and the exterior of an oral appliance. The system also includes one or more sensors mounted on the robotic dispensing device, the one or more sensors configured to detect a marker for registering a position and orientation of the oral appliance. The system further includes a processor configured to receive and process input from the one or more sensors; and a controller operatively connected to the processor and configured to operate the robotic dispensing device, at least in part, on input from the one or more sensors and processed by the processor, wherein the robotic dispensing device is configured to dispense from the outlet the medicament at discrete regions of an interior, an exterior or both the interior and the exterior of an oral appliance. In some embodiments, one or more medicaments are incorporated into a hydrogel and loaded into an oral appliance by using the robotic dispensing device described in this application.

In other aspects, an oral appliance for delivering a medicament to an oral cavity is provided. The oral appliance comprises an exterior and an interior, the interior of the oral appliance configured to contour at least a portion of teeth and/or soft tissue areas of the oral cavity. The oral appliance also includes a marker on the exterior, interior or both the exterior and interior of the oral appliance, the marker for registering the position and orientation of the oral appliance with a robotic dispensing device; and a projection and/or recess configured for manipulation of the oral appliance.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings.

Figure 1:
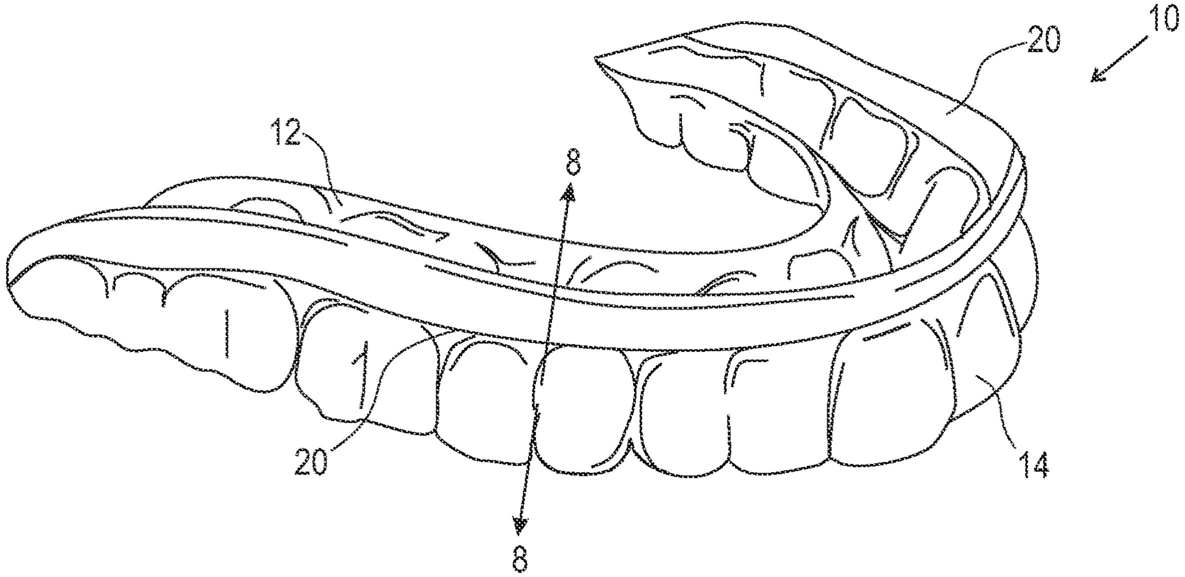
FIG. 1 illustrates an enlarged side view of an embodiment of the oral appliance covering the teeth and/or soft tissues of a patient, the oral appliance without teeth and/or soft tissues inserted in the oral appliance.

It is to be understood that the figures are not drawn to scale. Further, the relationship between objects in a figure may not be to scale and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a medicament" includes one, two, three or more medicaments.

The term "porous" as used herein, refers to a material which is permeable such that fluids are movable therethrough by way of pores or other passages. An example of a porous material is a hydrogel material, concrete, cellulosic material, ceramics, foams, sponges, combinations thereof and/or derivatives thereof. The porous material may be the result of using a low or high molecular weight polymer. In some embodiments, the polymer may be porous as it is dispensed at a low density on the oral appliance and/or substrate, or is dispensed in a geometric pattern, either as a specific structure or a randomized structure.

The term "non-porous" as used herein, refers to a material which is impermeable such that fluids cannot move through the material. The non-porous material may be the result of using a low or high molecular weight polymer. In some embodiments, the polymer may be non-porous as it is dispensed at a high density on the oral appliance and/or substrate in a solid form with no structural spacing to hold medicaments, as described above.

The term "hydrogel" or "hydrogels" refer to a broad class of polymeric materials, that may be natural or synthetic, which have an affinity for an aqueous medium (e.g., a medicament), and are able to absorb aqueous medium.

The term "medicament" as used herein, is generally meant to refer to any substance that alters in part or in toto the physiology of a patient. The term "medicament" may be used interchangeably herein with the terms “medicine”, “drug”, “therapeutic agent”, “therapeutically effective amount”, or “active pharmaceutical ingredient”. It will be understood that a “medicament formulation” may include more than one therapeutic agent, wherein exemplary combinations of therapeutic agents include a combination of two or more medicaments.

The terms, “treating” or “treatment” includes “preventing” or “prevention” of disease. In addition, “treating” or “treatment” does not require complete alleviation of signs or symptoms, does not require a cure, and specifically includes protocols that have only a marginal effect on the patient.

The term “localized” delivery includes delivery where one or more medicaments contact the tooth and/or soft tissue areas, for example, the gingival margins of the teeth or a region inside of the mouth such as the palate, or in close proximity thereto.

The term “targeted delivery” includes delivery of one or more medicaments at the target site as needed for treatment of the disease or condition including cosmetic applications, for example, whitening teeth or removing stains. In some embodiments, the oral appliance can be used to deliver medicament to the soft tissue of the inside of the mouth including, but not limited to, any soft tissue adjacent or between the teeth including, but not limited to, the papilla, tissue of the upper and lower dental arches, marginal gingiva, gingival sulcus, inter-dental gingiva, gingival gum structure on lingual and buccal surfaces up to and including the muco-gingival junction and/or the palate and/or the floor of the mouth. In various embodiments, the soft tissue area includes the muco-buccal folds, hard and soft palates, the tongue, lining mucosa, and/or attached gingival tissue.

The term “custom fit” as used herein, refers to an oral appliance that is specifically made via molding, 3D printing or any way, to correspond to at least a portion of a tooth, a selected number of teeth, all of the teeth and/or soft tissues found in the mouth of a specific individual patient. A custom fit oral appliance is not a generic device which is then heated or otherwise manipulated by a consumer, inserted into their mouth by themselves and then molded by that consumer to fit their own mouth. The patient image is the result of an action upon that particular individual by another person whereas the consumer is acting upon himself/herself by manually manipulating the generic material.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under anyone heading may be used in conjunction with embodiments under any other heading.

Oral Appliance

Numerous custom fit oral appliances can be made in a variety of ways including by traditional thermoforming, 3D printing or additive manufacturing, or injection molding or other ways. Unlike orthodontic appliances, the present oral appliance is not designed to move teeth and is not an orthodontic appliance. Therefore, a plurality of oral appliances will be configured to fit the teeth in the same position as was imaged within the oral appliance. The teeth position will not change. However, the medicament disposed in or on the oral appliance will be in the same or different areas at different stages of the treatment regimen with a variety of oral appliances. Thus, kits containing a plurality of oral appliances can be provided with different treatment plans. For example, as the patient condition improves, each oral appliance will have a decreasing amount of medicament or the medicament can change as the treatment progresses. In some embodiments, the area targeted for treatment with a medicament can change based on how the treatment progresses.

In various embodiments, the oral appliance is monolithic or a single piece and the interior surface custom fit and formed to fit contours of the teeth and/or soft tissue areas inside the oral cavity of a patient in need of treatment. The device of the present application has the medicament dispensed into the device. In some embodiments, the medicament is not removable from it except by diffusion in the mouth. In certain embodiments, the oral appliance comprises, consists essentially of or consists of one, two, three, four, five or more oral appliances.

In various embodiments, the oral appliance is not monolithic or a single piece. The medicament is disposed on the inside and/or on the outside of the oral appliance, but as a separate component to the oral appliance. For example, the medicament can be disposed in porous material (e.g., polymer) that is configured to allow release of the medicament when the oral appliance is worn.

In some embodiments, oral appliances include, but are not limited to, oral trays, oral holders, oral covers, or the like that are designed to be placed within the oral cavity. The interior surface and/or exterior surface of the oral appliance contains a medicament disposed inside the porous portion of the polymer of the oral appliance and the medicament can be disposed anywhere within or on the oral appliance. In some embodiments, the exterior surface of the oral appliance is porous and allows medicament to be released to adjacent teeth and/or soft or hard tissue, or into the mouth in general. In some embodiments, the medicament and/or porous material can be monolithic with the device—that is the device, medicament and porous material are a single piece.

Numerous different oral appliances can be made by the methods of the present application, including custom fit oral appliances that correspond to a digital scan taken from the patient's mouth or impression molds. Custom fit oral appliances are generally described in U.S. Pat. No. 9,649,182 to Peter J. Zegarelli, filed Jun. 18, 2015. The entire disclosure of this patent is herein incorporated by reference into the present disclosure.

The oral appliance when worn allows the interior and/or exterior surface of the oral appliance to be adjacent to the teeth and/or gums or other tissue in the oral cavity. In some embodiments, the oral appliance receives one or more teeth including one or more molars, premolars, incisors, cuspids, tooth implants, or combinations or portions thereof.

The contact of the oral appliance with the tissue, when the oral appliance contains medicament in discrete regions, will allow medicament to be released from the oral appliance to the target tissue areas in the oral cavity (e.g., gum, gum line, teeth, etc.) at the desired regions adjacent to the medicament-containing discrete regions of the oral appliance. In this way, targeted therapy can be directed at the desired regions in the oral cavity. By providing an oral appliance with discrete medicament-containing regions and non-medicament-containing regions, medicament release can be controlled to adjacent tissue or confined to those regions adjacent to the non-medicament-containing material without dilution or contamination by oral fluids such as saliva or releasing the medicaments onto non-targeted areas of the mouth with sometimes deleterious effects.

In some embodiments, the medicament containing regions are porous and the non-medicament containing regions are non-porous. In some embodiments, the oral appliance is predominantly porous (at least 51% or more) and non-porous material is coated on the oral appliance at discrete regions to make these discrete regions non-porous. In this way, medicament loading of the oral appliance and medicament release from the oral appliance is controlled as medicament will be released from the porous material at discrete regions and can target specific tissues in the oral cavity.

In some embodiments, the oral appliance is predominantly non-porous (at least 51% or more) and porous material containing medicament is dispensed into the oral appliance at discrete regions to make these discrete regions porous. In this way, medicament loading of the oral appliance and medicament release from the oral appliance is controlled as medicament will be released from the porous material at discrete regions and can target specific tissues in the oral cavity.

It will be understood that the medicament can be mixed with the polymer before, during or after the manufacture of the oral appliance.

In some embodiments, the oral appliance is made from a porous material that contains the medicament, and an agent that reduces porosity is applied to one or more discrete regions of the porous material to make the one or more discrete regions of the oral appliance non-porous as more particularly described in U.S. patent application Ser. No. 15/895,554 to Peter J. Zegarelli, filed on Feb. 13, 2018. The entire disclosure of this application is incorporated herein by reference into the present application. For example, a cross-linking agent can be used to reduce porosity of a porous oral appliance and make that region where the crosslinking agent is applied to non-porous to reduce or eliminate medicament release from that region.

In some embodiments, the oral appliance can be made by controlling the print density of the polymer during 3D printing or additive manufacturing. For example, the same polymer can be printed (e.g., using the same print head) at a density of, for example, 0.25 g/cm$^3$ to 0.5 g/cm$^3$ at discrete regions to form the porous regions of the oral appliance and at a higher density for example, 0.8 g/cm$^3$ to 1.5 g/cm$^3$ to make the oral appliance non-porous at discrete regions. This will be one way to produce the oral appliance without medicament and then the robotic device can dispense the medicament at discrete regions of the oral appliance. In some embodiments, the medicament can be disposed in a porous material such as a hydrogel.

In some embodiments, the oral appliance can be made by controlling the density of the polymer during 3D printing or additive manufacturing. For example, different polymers can be printed using two or more print heads, each print head having a different polymer. A high-density polymer can be used (e.g., 50,000 MW) and printed at discrete regions to form the non-porous regions of the oral appliance and another print head can use a low-density polymer (e.g., 5,000 MW) to make the oral appliance porous at discrete regions.

It will be understood that the oral appliance with discrete portions of the porous material and with discrete portions of non-porous material can be monolithic or a single piece having the same or different material. This type of oral appliance, in some embodiments, does not contain a porous insert after the oral appliance is made. Such porous inserts are described in U.S. Pat. No. 9,579,178, filed Jul. 12, 2013 to Peter J. Zegarelli. The entire disclosure of this patent is herein incorporated by reference into the present disclosure.

In some embodiments, methods, systems and apparatuses for the generally continuous production of a three-dimensional oral appliance are provided. In these methods, systems and apparatuses, the three-dimensional oral appliance can be produced from a liquid interface, which is often referred to as "continuous liquid interphase printing", which are suitable methods, systems and apparatuses for making the oral appliance. Suitable operation parameters for the continuous production of the oral appliance using 3D printing technology is described in U.S. Pat. No. 9,205,601 assigned to Carbon3D, Inc. The entire disclosure of this patent is herein incorporated by reference into the present disclosure. This will be one way to produce the oral appliance without medicament and then the robotic device can dispense the medicament at discrete regions of the oral appliance.

Figure 2:
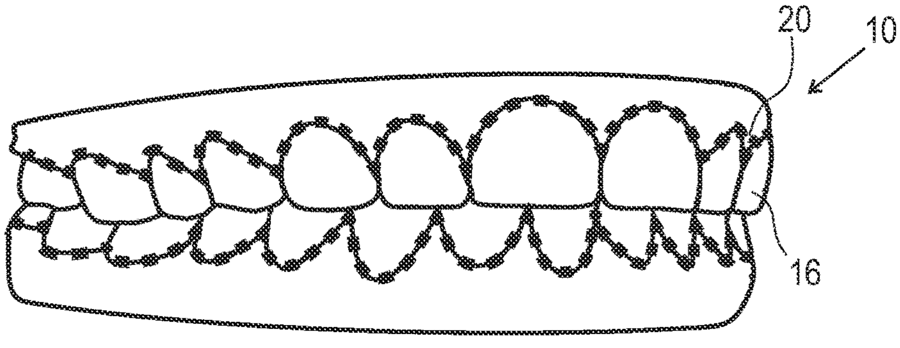
FIG. 2 illustrates an enlarged side view of an embodiment of the oral appliance, where the medicament is shown as infused polymer gel layer that is adjacent to the gingival sulcus region. This view has the teeth and gums loaded in the interior surface of the oral appliance and the oral appliance can be transparent or non-transparent.

Referring to FIGS. 1-3, an enlarged side view of an embodiment of the oral appliance 10 is illustrated. The oral appliance has an interior surface 12 and exterior surface 14, both comprising, in some embodiments, a polymer. The interior surface 12 contacts one or more teeth and/or soft tissue areas of a patient. The interior surface 12 is custom fit to the individual patient's mouth and configured to contour at least a portion of teeth and/or soft tissues of the oral cavity. In this view the interior surface 12 contacts the teeth and soft tissue. Oral appliances include, but are not limited to, oral trays, oral holders, oral covers, or the like that are designed to be placed within the oral cavity. The interior surface 12 and/or exterior surface 14 of the oral appliance contain a medicament disposed in or on the polymer and the medicament can be disposed anywhere within or on the oral appliance. For example, the medicament can be disposed at discrete regions adjacent to the treatment area or uniformly disposed throughout the device. As the interior and/or exterior surface of the oral appliance contacts the oral cavity, the medicament is released from the polymer (e.g., gel or hydrogel) by all or parts of the oral appliance contacting the desired treatment site or pressure from the device contacting tissue or fluid at the treatment site (e.g., gums, tissue, teeth, etc.).

In some embodiments, polymer containing medicament can degrade over time by the action of enzymes, by hydrolytic action and/or by other similar mechanisms in the oral cavity. In some embodiments, all or discrete portions of the polymer containing medicament will degrade and release medicament at or near the target site in the oral cavity. The oral appliance will cover at least a portion of the teeth and or gums by applying the device over axis 8-8 to cover the area of the teeth and or gums, and the oral appliance will be adjacent to the gingival sulcus 20, which will allow the medicament, if desired, to be released from the polymer to this area.

FIG. 2 is an enlarged side view of an embodiment of an oral appliance. In this embodiment, the oral appliance is transparent, colored, translucent or opaque and holds teeth 16 and or gums, which are covered by it. The oral appliance comprises a surface that contains medicament as part of the polymer that in use releases the medicament at or near the gingival sulcus 20.

Oral appliance 10 can also include at least a projection 24 and/or recess configured for manipulation of the oral appliance by a robotic device as illustrated in FIGS. 3A, 3B, 3C and 3D. In some aspects, projection 24 comprises at least a handle with or without a gripping surface 26 or a combination thereof configured to mate with the robotic arm of a robotic dispensing device. In some embodiments, projection or handle 24 can also be used to manipulate oral appliance 10 manually. Incorporating at least a handle with or without a gripping surface into the oral appliance of this disclosure facilitates the robotic maneuvering of the oral appliance so that its geometry and structural integrity does not get compromised by the robot's squeezing or handling of it.

Figure 3A:
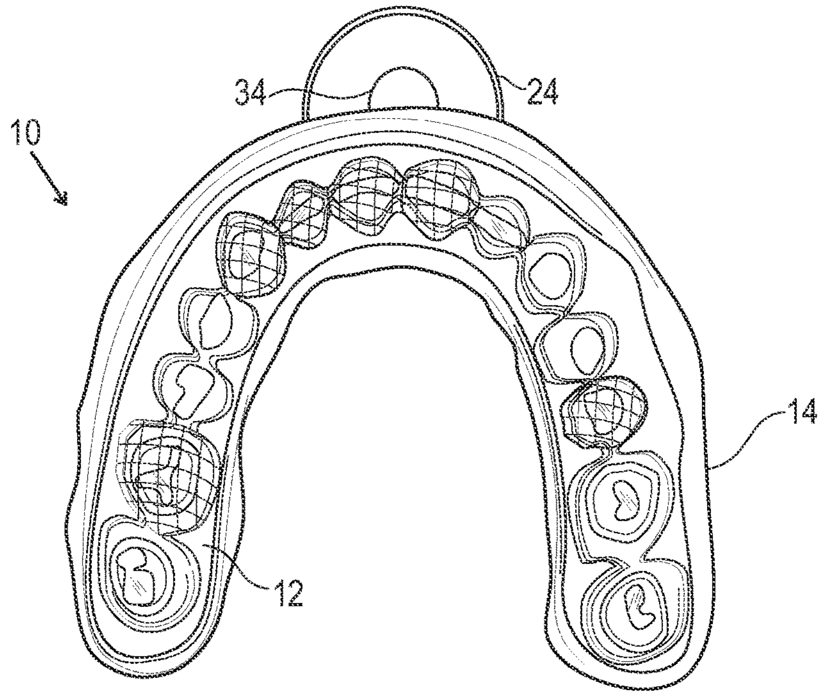
FIG. 3A illustrates a top view of the oral appliance of FIG. 1, the oral appliance having a handle and covering the lower teeth and/or soft tissues of a patient.
Figure 3B:
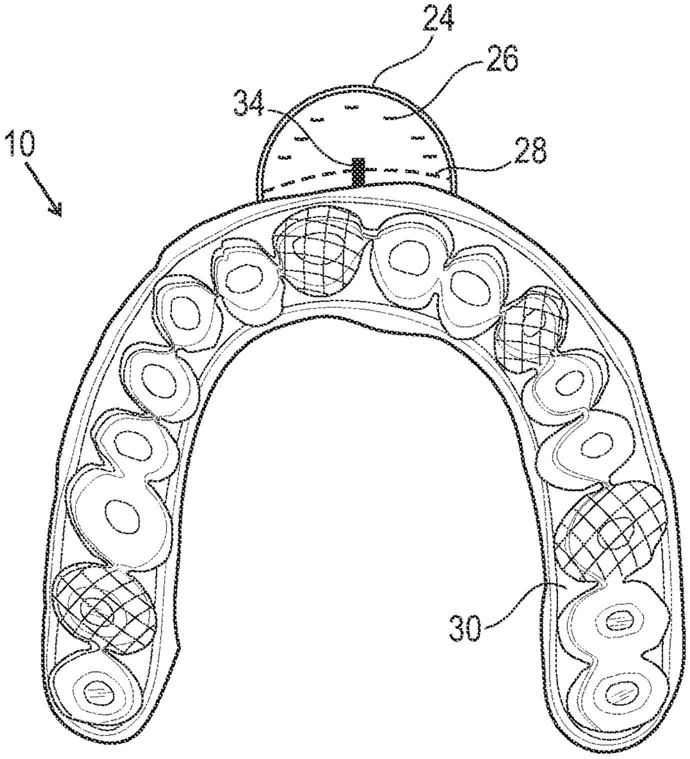
FIG. 3B illustrates a bottom view of the oral appliance of FIG. 1, the oral appliance having a handle with gripping surface and indentation covering the lower teeth and/or soft tissues of a patient.
Figure 3C:
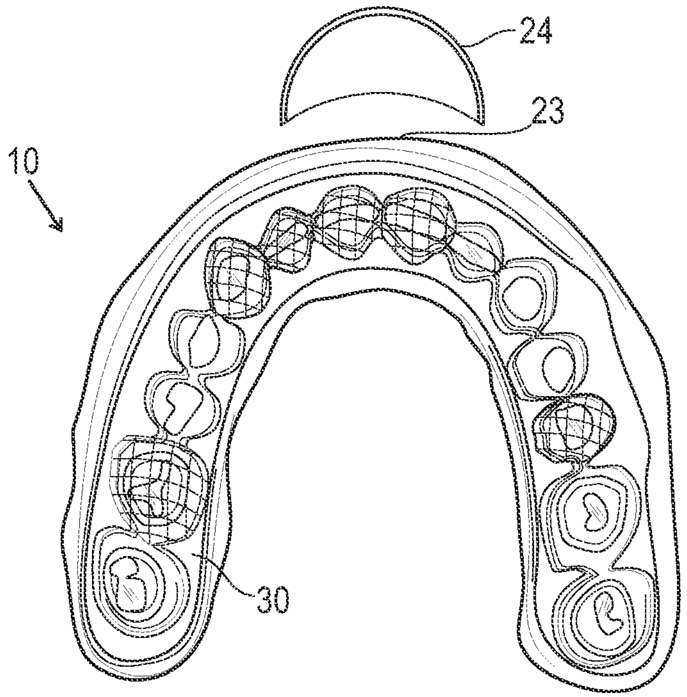
FIG. 3C illustrates a top view of the oral appliance of FIG. 1, the oral appliance having a separated handle and covering the lower teeth and/or soft tissues of a patient.

In other aspects, projection 24 is removable via a separation assist, for example, indentation 28 as illustrated in FIG. 3B to separate entirely from oral appliance 10 as illustrated in FIG. 3C. In some aspects, the separation assist includes a score line to allow the projection and/or recess to be easily removed from the oral appliance. After the projection is removed, the surface 23 of the exterior of the oral appliance can be smoothed so as not to provide discomfort to the patient when the oral appliance is worn. It will be understood that although the projection 24 is shown on the exterior surface of the oral appliance, the projection can be positioned on the interior surface or a combination of the exterior surface and the interior surface. In some embodiments, the projection can have a different stiffness compared to the other parts of the oral appliance. For example, the projection can be less flexible as compared to the remainder of the oral appliance so that it is easier to break (e.g., break away) or separate the projection from the oral appliance. The projection 24 can also be manually removed or machined off in toto or in part. Further the handle can be left on the oral appliance and serve a second purpose—as an assist to patients as a grabber or handle for the patient to hold onto the oral appliance and insert the appliance into the mouth and onto the teeth and soft tissues. Further, the handle can be used as an assist for the patient to remove the oral appliance from onto the teeth and soft tissues and out of the mouth. This handle would be especially valuable to those patients with motor skill deficits and/or neurologic disorders and/or to caregivers of compromised patients.

Figure 3D:
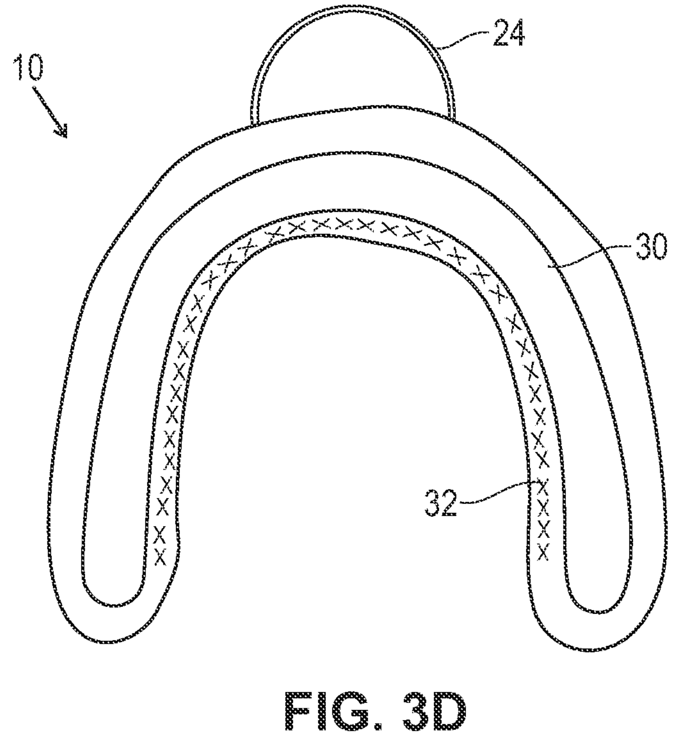
FIG. 3D illustrates a bottom view of the oral appliance of FIG. 1, the oral appliance having a handle and a barrier and covering the lower teeth and/or soft tissues of a patient.

In various embodiments, the oral appliance includes channel 30 configured to receive the medicament from the outlet of a robotic dispensing device as illustrated in FIG. 3D. In some embodiments, channel 30 can be continuous in the interior of the oral appliance and extend along a gum line perimeter. In other embodiments, the oral appliance includes barrier 32 for providing a seal between channel 30 and at least a portion of the teeth and/or soft tissue areas of the oral cavity to prevent or reduce leaching of the medicament from the oral appliance as illustrated in FIG. 3D.

In various embodiments, oral appliance 10 includes a zero point or other reference marker 34 that can be placed on the oral appliance and/or on handle 24 or gripping surface 26 of oral appliance 10 for registering its position relative to the robotic dispensing device. Using a zero-point marker facilitates orienting the oral appliance in space in three dimensions during the precision medicament dispensing process. To promote a precise, automated robotic dispensing of hydrogel in oral appliance 10, X, Y, Z Cartesian coordinates of the patient specific customized channel are created along the anatomic geometry of the patient's oral cavity such that a robot can read the coordinate data points in width, length and depth and create an accurate guideline to dispense precisely a hydrogel strip, bead or reservoir onto or into the oral appliance. Thus, each tooth, gum line and/or other portions of the oral appliance and/or oral cavity can be defined by X, Y, Z Cartesian coordinates to form a guideline for guiding the robotic arm of the robotic dispensing device to dispense the medicament at discrete regions of the oral appliance. For example, in one embodiment, each tooth can be defined by at least 10 Cartesian X, Y, Z coordinates. In some embodiments, the dispensing arm is stationary and the oral appliance is moved in three dimensions in space by the robotic arm attached to the oral appliance such that the dispensing arm is in the vertical position to facilitate the dispensing of material.

Figure 4:
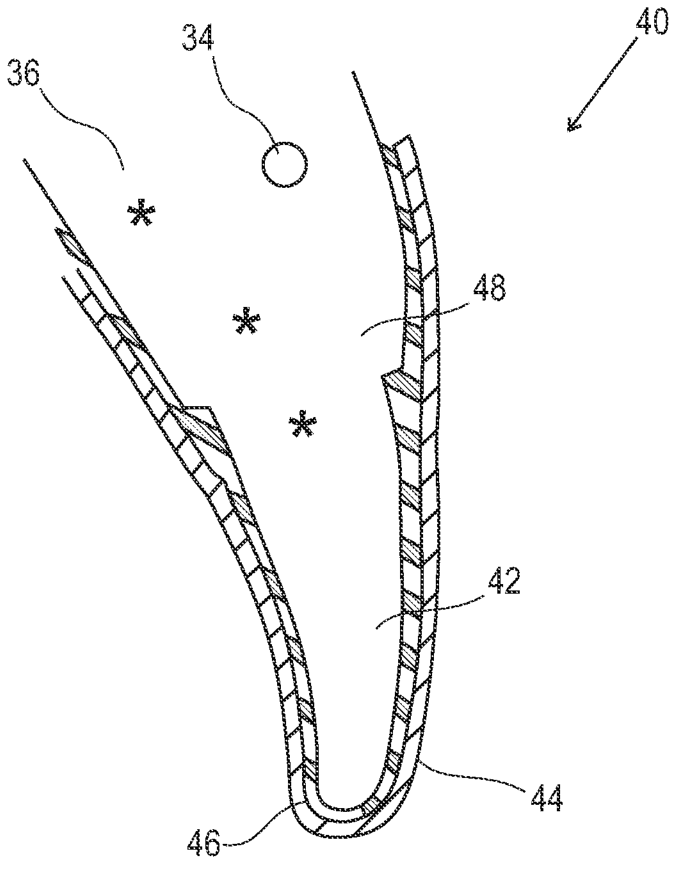
FIG. 4 illustrates an enlarged side cross sectional view of an embodiment of the oral appliance configured to correspond to and cover the tooth and soft tissue areas inside the oral cavity. The interior surface encompasses the polymer gel material having the medicament.

FIG. 4 illustrates an enlarged side cross sectional view of an embodiment of the oral appliance 40 showing an outline of a tooth 42. The oral appliance 40 has an exterior surface 44 and interior surface 46. The interior surface of oral appliance 40 contains a medicament infused polymer gel or hydrogel, which contacts tooth 42 up to gingival area 48. In the embodiment shown, the medicament in the polymer layer extends and contacts the buccal surfaces of the teeth and surrounding gingival tissue and over adjacent gingival tissue on a lingual side of the teeth. In some embodiments, the oral appliance extends over occlusal surfaces of the teeth and/or over lingual surfaces of the teeth in need of treatment. There are several locations 34 on tooth 42 where a zero-point marker can be located. In other aspects, each tooth can have a plurality of reflective markers 36, for example, attached to the tooth image to guide the robotic arm of a robotic dispensing device. Markers can be placed on other sites of the oral cavity, for example, on the buccal side, the lingual side and the occlusal side. More markers can be deployed if the tooth and/or soft geometries are not constant or if required due to a particular situation in a case.

Figure 4A:
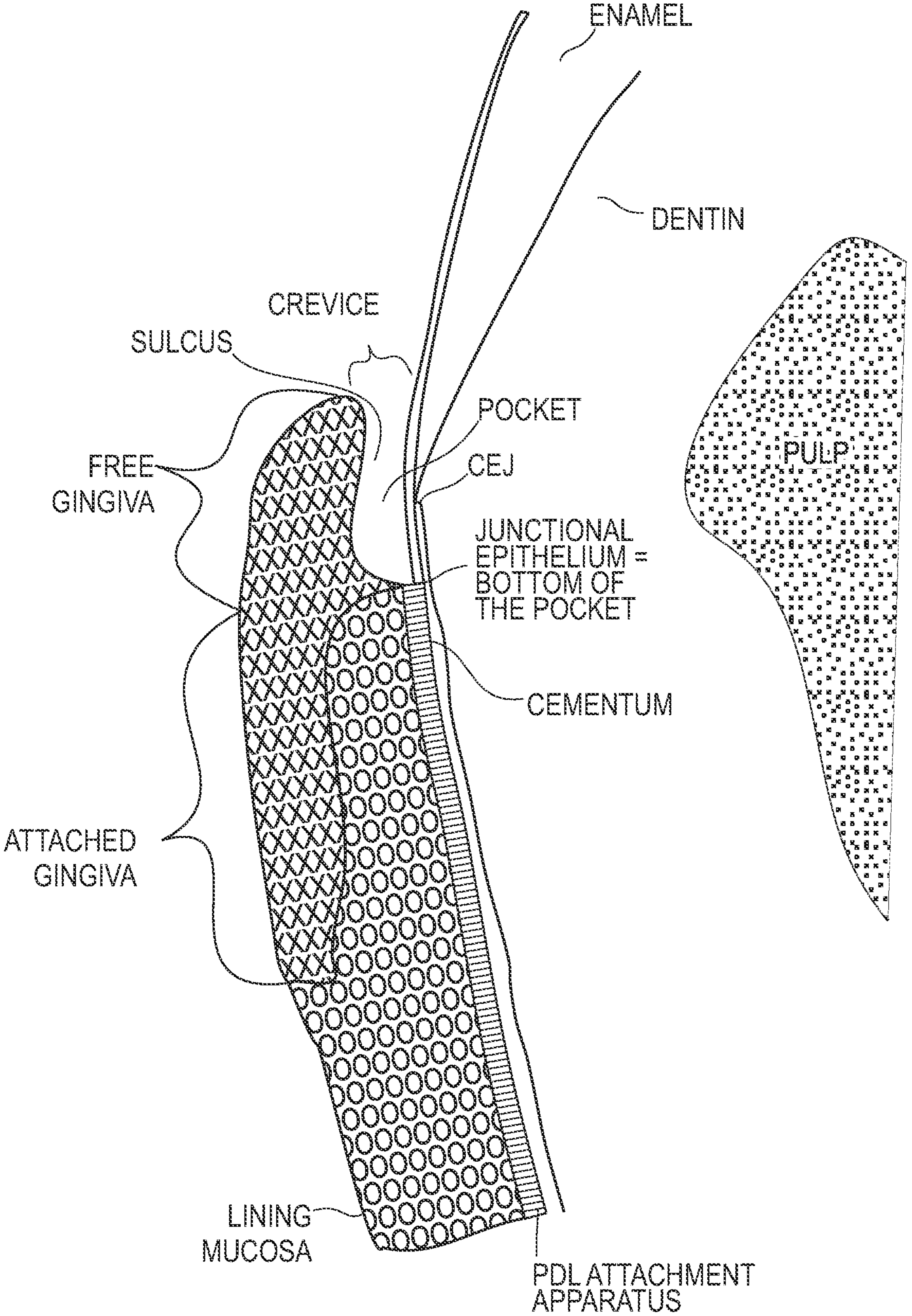
FIG. 4A illustrates an enlarged cross-sectional view of the anatomy of the gums and a tooth including free gingiva, attached gingiva, lining mucosa, the periodontal pocket or crevice, the cementoenamel junction (CEJ), periodontal ligament, cementum, the enamel, dentin, pulp and the junctional epithelium. In some embodiments, the treatment area is the periodontal pocket that is targeted for delivery. The design of the medicament of the oral appliance is to target the periodontal pocket or crevice of the sulcus and extrude the medicament into the entrance of the periodontal pocket. The robotic device can dispense medicament so precisely in the oral appliance to specifically target the periodontal pocket or crevice.

FIG. 4A illustrates an enlarged cross-sectional view of the anatomy of the gums and a tooth including free gingiva, attached gingiva, lining mucosa, the periodontal pocket or crevice, the cementoenamel junction (CEJ), periodontal ligament, cementum, the enamel, dentin, pulp and the junctional epithelium. In some embodiments, the treatment area is the periodontal pocket that is targeted for delivery. The design of the medicament of the oral appliance is to target the periodontal pocket or crevice of the sulcus and extrude the medicament into the entrance of the periodontal pocket. The robotic device can dispense medicament so precisely in the oral appliance to specifically target the periodontal pocket or crevice.

Figure 4B:
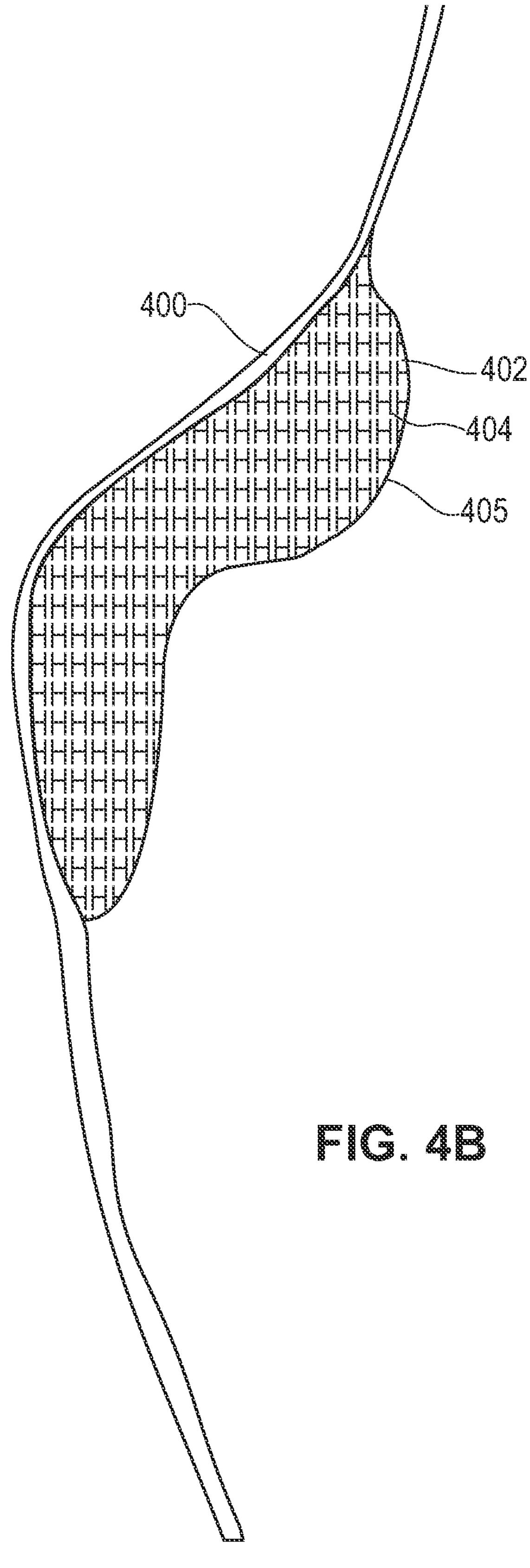
FIG. 4B illustrates an enlarged cross-sectional view of a portion of the oral appliance. In the embodiment shown, medicament is disposed in a porous material that is a hydrogel and the robotic device dispenses medicament so precisely at a discrete region of the oral appliance. The hydrogel is shown in an uncompressed state and when worn with slight pressure, the hydrogel will be compressed against, among other things, the gingival crevice or periodontal pocket causing a seal of the entrance of the gingival crevice or periodontal pocket, which prevents oral fluids (e.g., saliva, exudate, other foreign liquids, etc.) from entering the crevice or pocket, which allows release of the medicament in the gingival crevice or periodontal pocket with minimal dilution from other mouth fluids such as saliva and allows the hydrogel to absorb or wick fluid from the crevice or pocket.

FIG. 4B illustrates an enlarged cross-sectional view of a portion of the oral appliance 400 that has medicament dispensed via a robotic outlet into the oral appliance. In the embodiment shown, medicament is disposed in a porous material 402 that is a hydrogel 404 and is dispensed precisely from the outlet of the robotic device at a discrete region of the oral appliance. The hydrogel is shown in an uncompressed state 405 and when worn with slight pressure, the hydrogel will be compressed against, among other things, the gingival crevice or periodontal pocket causing a seal of the entrance of the gingival crevice or periodontal pocket, which prevents oral fluids (e.g., saliva, exudate, other foreign fluids, etc.) from entering the crevice or pocket, which allows release of the medicament in the gingival crevice or periodontal pocket and allows the hydrogel to absorb or wick fluid from the crevice or pocket. In this embodiment, the hydrogel is dispensed from the robotic device and disposed at a discrete region of the oral appliance and is sized to be greater than the height, width, and length of the entrance of the periodontal pocket or crevice.

Figure 4C:
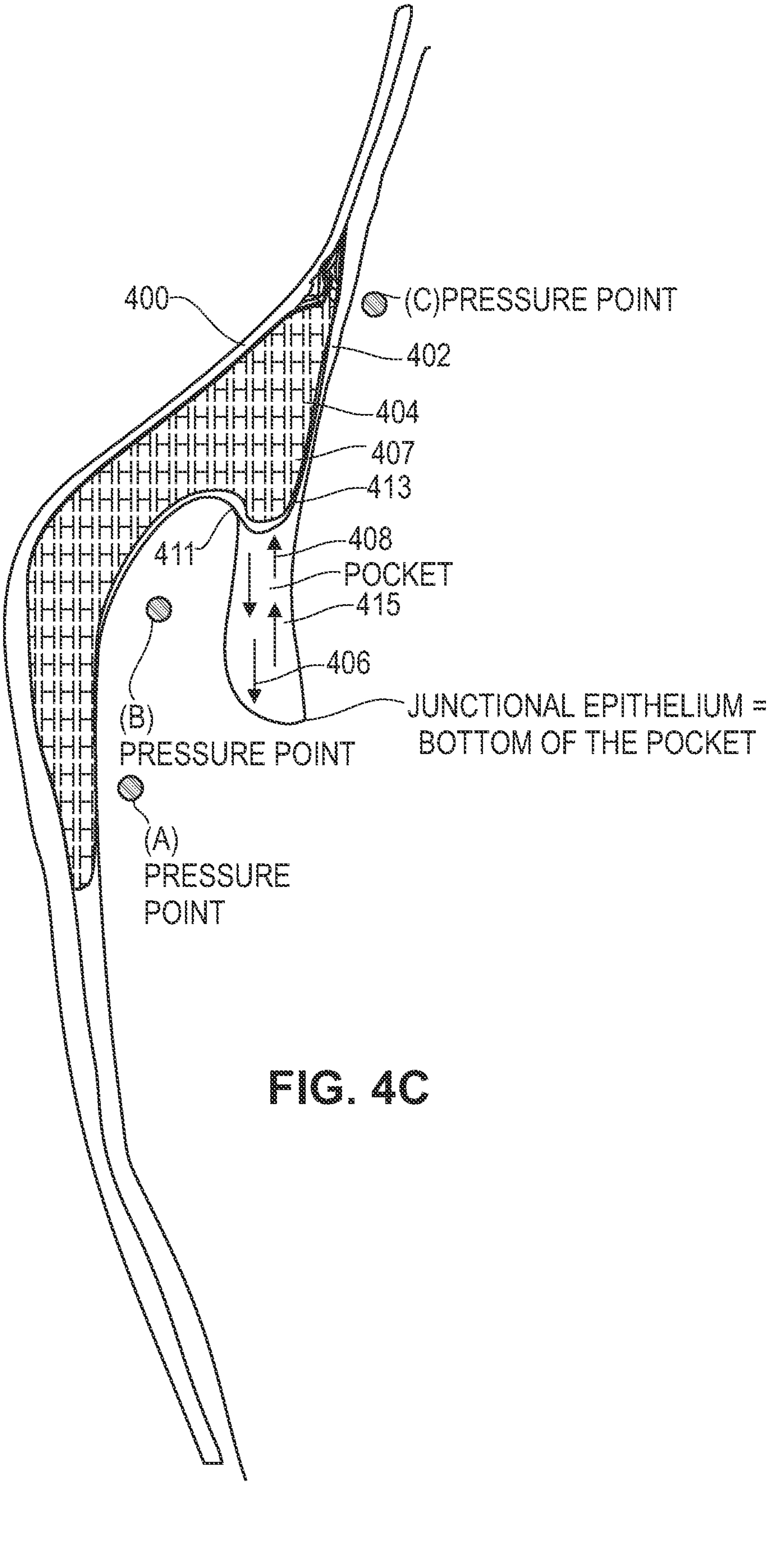
FIG. 4C illustrates an enlarged cross-sectional view of a portion of the oral appliance that is placed adjacent to the teeth and gums. In the embodiment shown, medicament is disposed in a porous material that is a hydrogel and the robotic device dispenses medicament so precisely at a discrete region of the oral appliance. The hydrogel is shown in a compressed state, where the device is worn and the hydrogel is compressed against, among other things, the treatment area, which is the gingival crevice or periodontal pocket causing a seal of the entrance of the gingival crevice or periodontal pocket, which prevents oral fluids (e.g., saliva, exudate, other foreign liquids, etc.) from entering the crevice or pocket. The hydrogel allows release of the medicament into the gingival crevice or periodontal pocket to treat the inflamed tissue shown by the down arrows. The hydrogel also absorbs or wicks oral fluids from the crevice or pocket, which aides healing, shown by the up arrows.

FIG. 4C illustrates an enlarged cross-sectional view of a portion of the oral appliance 400 being worn that is placed adjacent to the teeth and gums using the top down approach to treating periodontal disease as described in International application No. PCT/US2020/059440 filed on Nov. 6, 2020, incorporated herein by reference in its entirety. In the embodiment shown, medicament has been precisely dispensed via a robotic outlet into the oral appliance and the medicament is disposed in a porous material 402 that is a hydrogel 404 at a discrete region of the oral appliance. The hydrogel is shown in a compressed state 407, where the device is worn and the hydrogel is compressed against, among other things, the gingival crevice or periodontal pocket causing a seal 413 of the entrance of the gingival crevice or periodontal pocket, which prevents oral fluids (e.g., saliva, exudate, other foreign fluids, etc.) from entering the crevice or pocket. There is a gap 415 between the junctional epithelium and the entrance 411 of the crevice or pocket, which is now sealed by the hydrogel. This gap allows the hydrogel to release medicament in the gingival crevice or periodontal pocket to treat deep down into the inflamed tissue. The medicament release is shown by the down arrows 406. The hydrogel also absorbs or wicks oral fluids from the crevice or pocket which aides healing, shown by the up arrows 408. The hydrogel has dual ability to deliver medicament and wicking action to remove crevicular/sulcular fluids from the environment. This dual action of wicking which then creates a negative crevicular fluid flow, allows the medicaments under pressure, shown by pressure points A, B and C, to enter the top portion of the pocket to fill the resultant negative pressure void, thus inserting the medicaments further into the pockets.

Oral Appliance Materials

The oral appliance can be made of any materials that can hold and release the medicament. In various embodiments, the material from which the oral appliance can be made from includes swellable polymers, such as, for example hydrogels, gels, polymer brushes or combinations thereof.

In some embodiments, suitable polymers for use to make the oral appliance include, for example, polyacrylates, polyamide-imide, phenolic, nylon, nitrile resins, petroleum resins, fluoropolymers, copolyvidones (copovidones), epoxy, melamine-formaldehyde, diallyl phthalate, acetal, coumarone-indene, acrylics, acrylonitrile-butadiene-styrene, alkyds, cellulosics, polybutylene, polycarbonate, polycaprolactones, polyethylene, polyimides, polyphenylene oxide, polypropylene, polystyrene, polyurethanes, polyvinyl acetates, polyvinyl chloride, poly(vinyl alcohol-co ethylene), styrene acrylonitrile, sulfone polymers, saturated or unsaturated polyesters or combinations thereof.

In some embodiments, the polymer comprises, consists essentially of or consists of an amount from about 5% to about 100% by weight, from about 5%, 10%, 15%, 20%, 25%, 30%, 35%, 40%, 45%, 50%, 55%, 60%, 65%, 70%, 75%, 80%, 85%, 90%, 95% to about 100% by weight, from about 10% to about 15% by weight, from about 15% to about 20% by weight, from about 20% to about 25% by weight, from about 25% to about 30% by weight, from about 30% to about 35% by weight, from about 35% to about 40% by weight, from about 40% to about 45% by weight, from about 45% to about 50% by weight, from about 50% to about 55% by weight, from about 55% to about 60% by weight, from about 60% to about 65% by weight, from about 65% to about 70% by weight, from about 70% to about 75% by weight, from about 75% to about 80% by weight, from about 80% to about 85% by weight, from about 85% to about 90% by weight, from about 90% to about 95% by weight, or from about 95% to about 100% by weight of the oral appliance. In some embodiments, the oral appliance is substantially all polymer from about 80% to about 99.9% by weight. The medicament comprises, consists essentially of or consists of an amount from about 0.01% to about 50%, from about 0.1% to about 20% by weight, from about 0.5% to about 10%, or from about 1% to about 7% by weight of the oral appliance.

In various embodiments, the molecular weight of the polymer can be a wide range of values. The average molecular weight of the polymer can be from about 1000 to about 10,000,000 g/mol; or about 1,000 to about 1,000,000; or about 5,000 to about 500,000; or about 10,000 to about 100,000; or about 20,000 to about 50,000 g/mol.

In some embodiments, when the oral appliance is made from one polymer, the density of the polymer can vary such that the non-porous and porous regions are formed in the oral appliance from a single material.

In some embodiments, when different molecular weight polymers are used, the polymer can be dense and have a higher molecular weight such that the polymer is non-porous. In some embodiments, the polymer can be less dense and have a lower molecular weight such that the polymer is porous. In some embodiments, the oral appliance can be made from multiple polymers, as described above. The multiple polymers can have the same or different densities. The polymers can have an average molecular weight of from about 1000 to about 10,000,000 g/mol; or about 1,000 to about 1,000,000; or about 5,000 to about 500,000; or about 10,000 to about 100,000; or about 20,000 to about 50,000 g/mol.

The polymer can have a modulus of elasticity (Young's modulus) in the range of about $1\times10^{-2}$ to about $6\times10^{5}$ dynes/cm$^2$, or $2\times10^{4}$ to about $5\times10^{5}$ dynes/cm$^2$, or $5\times10^{4}$ to about $5\times10^{5}$ dynes/cm$^2$.

The polymer may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the polymer can comprise a hydrogel that is or is not infused with at least one medicament. Suitable hydrogels for use in the oral appliance, include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (for example, PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrolidone), acrylates such as poly(2-hydroxy ethyl methacrylate) and copolymers of acrylates with N-vinyl pyrolidone, N-vinyl lactams, polyacrylonitrile or combinations thereof.

In some embodiments, cross-linking agents used to make the porous material non-porous include, but are not limited to, glutaraldehyde, formaldehyde, epoxy, compounds, dialdehyde, sodium borate/boric acid, glyoxal, oxidized dextrins, epichlorohydrin, endogen polyamine spermidine, oxidized alginate, zinc, borax, ethylene glycol dimethacrylate (EGDMA), N,N'-methylenebisacrylamide, derivatives of ethylene glycol di(meth)acrylate, derivatives of methylenebisacrylamide, formaldehyde-free crosslinking agent including N-(1-Hydroxy-2,2-dimethoxyethyl) acrylamide, or a combination thereof.

In some embodiments, it may be difficult for the medicament to move in and out of the oral appliance. In some embodiments, a porosity reducing agent such as a cross-linking agent is used to generate a non-porous region on the polymer oral appliance.

In some embodiments, the oral appliance can be transparent, colored, translucent or opaque so that a user can see the teeth. The oral appliance may be disposable and sterilizable. In various embodiments, one or more components of the oral appliance is sterilized by radiation in a terminal sterilization step in the final packaging. Terminal sterilization of a product provides greater assurance of sterility than from processes such as an aseptic process, which require individual product components to be sterilized separately and the final package assembled in a sterile environment. Other methods may also be used to sterilize one or more components of the oral appliance, including, but not limited to, E-beam radiation, gamma radiation, gas sterilization, such as, for example, with ethylene oxide or steam sterilization.

Automated Dispensing Systems

Figure 5:
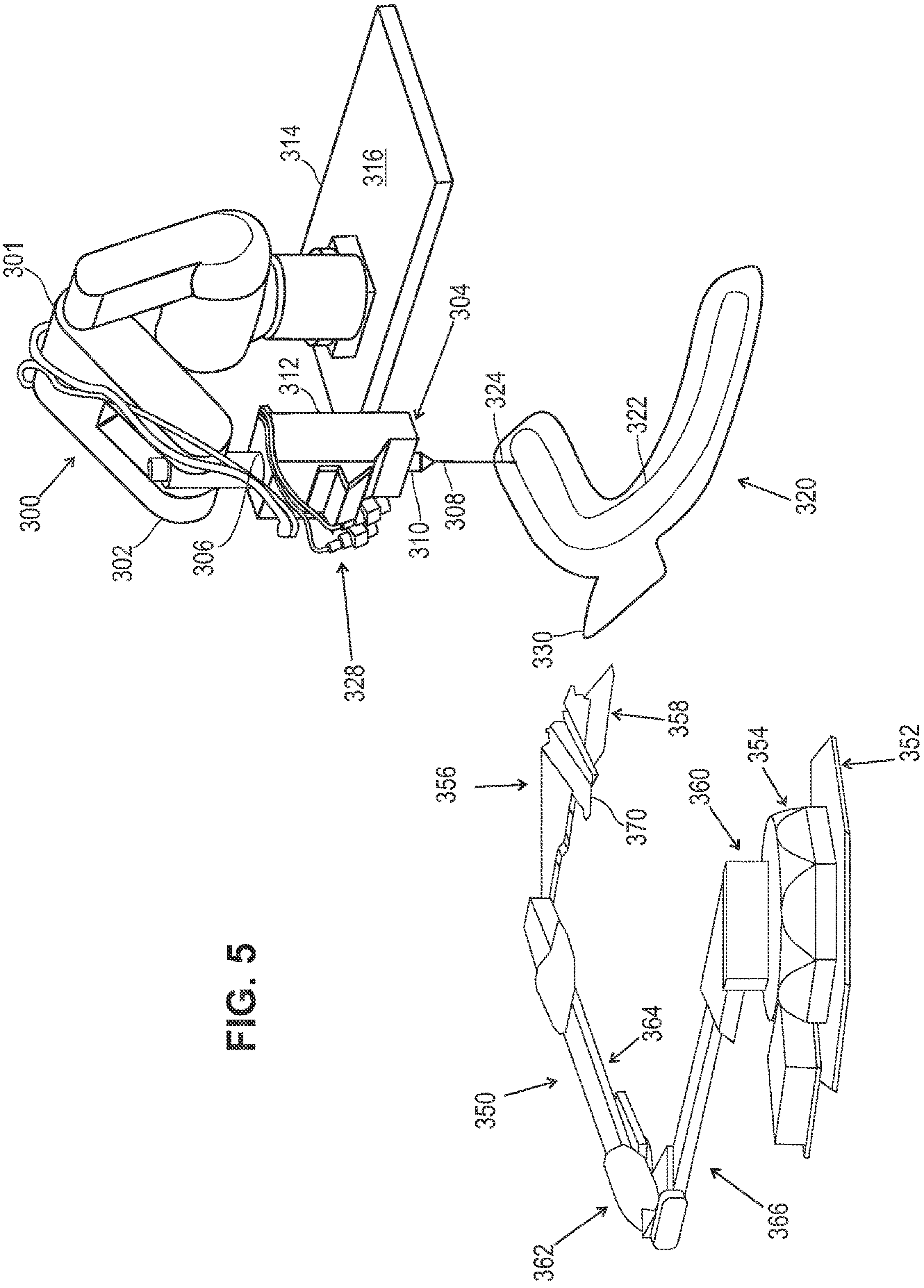
FIG. 5 illustrates a perspective view of a robotic system having a first and second robotic arms.

FIG. 5 depicts an embodiment of an image-guided robotic dispensing system 300. The image-guided robotic dispensing system 300 is shown with a robotic dispensing device 301, including a first robotic arm 302 with a delivery tool assembly 304 attached to a distal tool plate 306 of the first robotic arm 302. The delivery tool assembly 304 includes dispensing tool 308 extending from a tubular body 310, which in turn extends from a delivery tool housing 312 attached to the tool plate 306. In some embodiments, the zero point marker and/or the guideline can assist dispensing tool 308 in orienting the oral appliance so that the dispensing outlet shown as a dispensing tip 324 of dispensing tool 308 is frequently placed in a vertically down position relative to the oral appliance so as to maximize the natural gravitational flow and lessen the pressure needed to dispense the hydrogel from dispensing tip 324. In this manner, the oral appliance is continually advanced along a guideline or guidelines through the continued multi-angled rotation of the oral appliance while the dispensing tip 324 remains static on its vertical axis. The oral appliance can also be rotated such that the dispensing tip 324 is frequently perpendicular to the surface of the oral appliance that the dispensing tip is dispensing on to. The dispensing tip may move slightly, but this is a desirable position. It is recognized that other orientations are also possible. In some embodiments, the dispensing tip and the robotic arms orient the oral appliance to facilitate dispensing of the materials.

The first robotic arm 302 has a base 314 mounted on a stable platform 316. An oral appliance 320 having a channel 322 is positioned relative to the first robotic arm 302, so that a targeted channel 322 and/or targeted discrete regions into or onto oral appliance 320 is directly underlying the dispensing tip 324 of the dispensing tool 308. The actual dimensions of dispensing tool 308 (e.g., its respective inner and out diameters) may vary in accordance with different embodiments of this application, depending, for example, on the particular therapeutic dispensing procedure to be performed and/or the particular substances to be delivered into or onto the targeted region(s) of oral appliance 320. In various embodiments, the robotic dispensing system 300 includes one or more sensors 328 (e.g., cameras or other special relationship devices) (two are visible in FIG. 5) mounted on the delivery tool housing 312 (which in turn is mounted on the distal end tool plate 306 of the first robotic arm 302).

In particular, the first robotic arm 302 is maneuverable so that the dispensing tool 308 may be positioned proximate a targeted location on the oral appliance, wherein one or both of the processor and controller are configured to cause dispensing tip 324 of dispensing tool 308 to dispense a controlled delivery of desired material along the coordinates chosen and precisely the quantitative amounts to be dispensed at discrete regions or in channel 322 of oral appliance 320. In some embodiments, robotic dispensing system 300 preferably includes a user interface (not shown) that allows a system operator to input instructions relating to one or more of a location, an orientation and a depth of the dispensing tool 308. Such a user interface, additionally or alternatively, preferably allows a system operator to input instructions relating to a type, a quantity, or both, of the therapeutic substance to be delivered into a targeted region of oral appliance 320.

Various embodiments of the robotic dispensing system 300 may be configured for delivery of therapeutic substances including, but not limited to, all of the therapeutic substances described in this application, into or onto target regions of oral appliance 320. Towards this end, under image guidance and verification, at a desired location, embodiments of the robotic dispensing system 300 precisely (and repeatedly) position the oral appliance 320 at respective desired locations at, and in desired orientation(s) relative to dispensing tip 324 of the dispensing tool 308. Further, due to the continued guiding and orientation of the oral appliance relative to the generally vertical robotic arm and perpendicular orientation of the dispenser, the dispensed hydrogel may be in such gravitational positions that the hydrogel may flow away from the Dig2 channel it was dispensed in. Therefore, the viscosity of the hydrogel must be formulated such that it can flow out of the dispensing nozzle but remain in place without distortion according to the Dig2 data points. The hydrogel is then cured using curing lights, heating or such that it hardens and binds to the oral appliance. The curing may occur simultaneously to the dispensing or cured after the dispensing is finished. In some embodiments, curing can be initiated by heat, radiation, electron beams, or chemical additives. In other embodiments, curing can occur by thermosetting in the absence of additives.

A number of differing delivery tool assemblies 304 may be housed in delivery tool housing 312, with each delivery tool assembly 304 configured for operating in conjunction with, and under the common control of, robotic dispensing system 300. Relative motion of the dispensing tool 308 may be provided by movement of first robotic arm 302 relative to oral appliance 320. Additionally, or alternatively, relative motion of the dispensing tool 308 to oral appliance 320 may be provided by embodiments of the delivery tool assembly 304. Regardless of how such relative motion of the dispensing tool 308 is accomplished, the respective delivery tool assemblies 304 are configured to deliver precisely metered doses or amounts of flowable substances into the targeted regions of the oral appliance.

In various embodiments, robotic dispensing system 300 illustrated in FIG. 5 also includes a second robotic arm 350 for holding and/or manipulating oral appliance 320 in position(s) effective to receive material from a dispensing tool 308. Second robotic arm 350 is supported on base 354 located on platform 352. Second robotic arm 350 has several articulated joints and arms configured to precisely maneuver second robotic arm 350 in at least six degrees of freedom, and/or a six-axis robot. Second robotic arm 350 includes a gripper or hand 358 that can grip projection or handle 330 of oral appliance 320. Gripper 358 is connected to a wrist 356, which in turn is connected to elbow 362 and shoulder 360 through forearm 364 and upper arm 366, respectively. In various embodiments, second robotic arm 350 includes one or more sensors 370 (e.g., cameras) mounted between gripper 358 and wrist 356. It is also recognized that the gripper may grab the tray directly without a projection or handle.

A processor (not shown in FIG. 5) associated with the robotic dispensing system 300 receives and processes images acquired by the one or more sensors. The robotic dispensing system 300 includes a controller (also not shown in FIG. 5) that is operatively associated with the processor and configured to precisely maneuver the first and second robotic arms 302 and 350 in six degrees of freedom and gripper 358 based, at least in part, on images acquired by the one or more sensors 328 and/or 370 and processed by the processor. It will be understood that although two robotic arms are shown, the dispensing and oral appliance manipulation can be accomplished with one robotic dispensing device 301 having one robotic arm.

Figure 6:
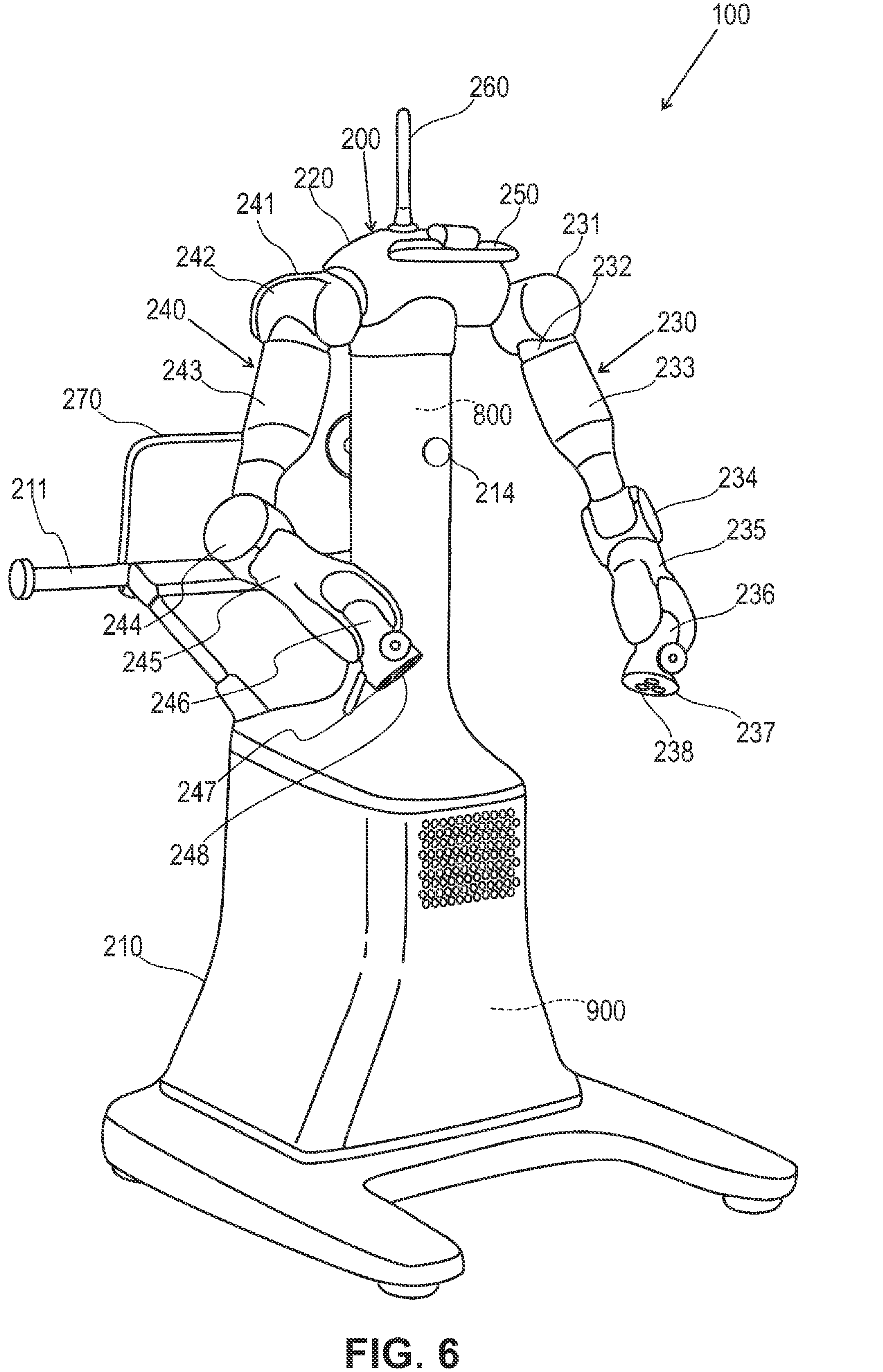
FIG. 6 illustrates a perspective view of a dual arm robot.

In another embodiment, a two-arm robot as described in U.S. Pat. No. 10,300,597 assigned to Seiko Epson Corporation can be used, incorporated herein by reference, and configured to use one robotic arm for holding an oral appliance and the other robotic arm for dispensing a therapeutic formulation into or onto the oral appliance. FIG. 6 illustrates robot 100 which has a main body 200, and a robot control device 900 for controlling the action of the robot main body 200. The robot main body 200 has a base 210, a body 220 connected to the base 210, a pair of articulated arms 230, 240 connected to both sides of the body 220, a first sensor 250 (e.g., stereo camera) and a second sensor 260 (e.g., signal light) provided to the body 220, a hand camera (not shown) provided to each of the articulated arms 230, 240, and a monitor 270 disposed on a rear side of the body 220.

The base 210 is provided with a plurality of wheels (rotating members) for making the movement of the robot 100 easy, a lock mechanism (not shown) for locking each of the wheels, and a handle (a grip section) 211 to be gripped when moving the robot 100. By releasing the lock mechanism and then gripping the handle 211 to push or pull the handle 211, the robot 100 can be moved at will, and by locking the wheels with the lock mechanism, the robot 100 can be fixed at a predetermined position. Base 210 is also provided with an emergency stop button 214. Body 220 is connected to the base 210 through an elevating mechanism 800 which enables body 220 to move up and down in a vertical direction. In some embodiments, body 220 is connected to base 210 via a joint mechanism which enable the body to be also rotatable around its vertical axis.

As shown in FIG. 6, articulated arm 230 includes a first shoulder section (a first arm) 231 connected to the body 220 via a joint mechanism (not shown), a second shoulder section (a second arm) 232 connected to the first shoulder section 231 via another joint mechanism (not shown), an upper arm section (a third arm) 233 connected to the tip of the second shoulder section 232 via a twist mechanism (not shown), a first lower arm section (a fourth arm) 234 connected to the tip of the upper arm section 233 via a joint mechanism (not shown), a second lower arm section (a fifth arm) 235 connected to the tip of the first lower arm section 234 via another twist mechanism (not shown), a wrist section (a sixth arm) 236 connected to the tip of the second lower arm section 235 via a joint mechanism (not shown), and a connector section (a seventh arm) 237 connected to the tip of the wrist section 236 via a twist mechanism (not shown). Further, the connector section 237 is provided with a hand section 238, and an end effector 610 corresponding to the operation to be performed by the robot 100 is attached to the hand section 238 via a kinesthetic sensor 740 as shown in FIG. 7.

The articulated arm 240 has substantially the same configuration as the configuration of the articulated arm 230 described above. Specifically, as shown in FIG. 6, the articulated arm 240 includes a first shoulder section (a first arm) 241 connected to the body 220 via a joint mechanism (not shown), a second shoulder section (a second arm) 242 connected to the first shoulder section 241 via another joint mechanism (not shown), an upper arm section (a third arm) 243 connected to the tip of the second shoulder section 242 via a twist mechanism (not shown), a first lower arm section (a fourth arm) 244 connected to the tip of the upper arm section 243 via a joint mechanism (not shown), a second lower arm section (a fifth arm) 245 connected to the tip of the first lower arm section 244 via another twist mechanism (not shown), a wrist section (a sixth arm) 246 connected to the tip of the second lower arm section 245 via a joint mechanism 560, and a connector section 247 connected to the tip of the wrist section 246 via a twist mechanism (not shown). Further, the connector section 247 is provided with a hand section 248, and an end effector 620 corresponding to the operation to be performed by the robot 100 is attached to the hand section 248 via a kinesthetic sensor 750 as shown in FIG. 7.

Figure 7:
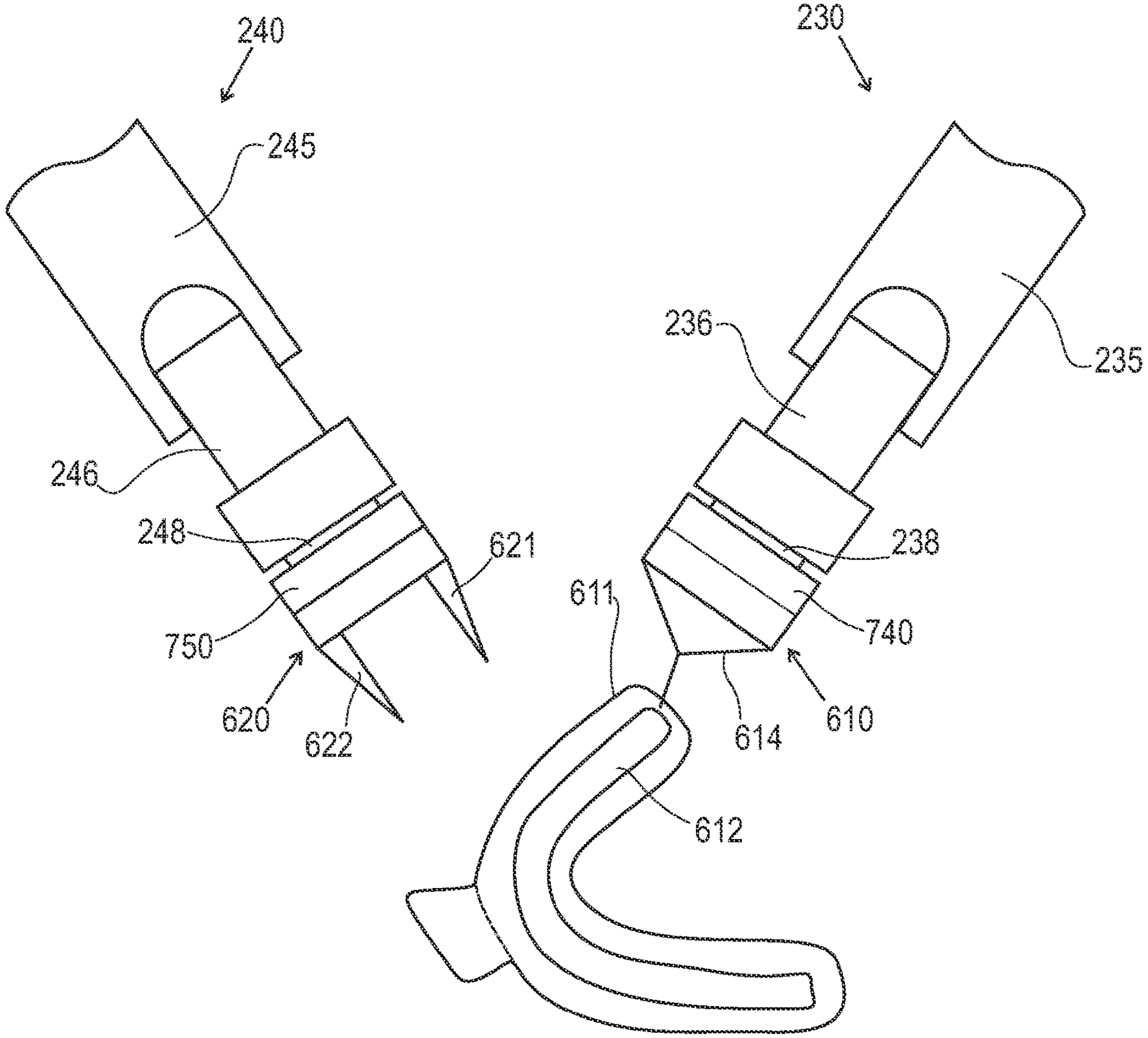
FIG. 7 is a diagram showing end effectors attached to the robot shown in FIG. 6.

As illustrated in FIG. 7, end effectors 610, 620 are attached to the tips of the respective articulated arms 230, 240 and have a function of, for example, gripping an object, for example, oral appliance 611. The configuration of each of the end effectors 610, 620 varies by the operation to be performed. For example, it is possible to adopt a configuration at end effector 620, having a first finger 621 and a second finger 622 configured to grip oral appliance 611. At end effector 610, the configuration can be changed and adapted to contain a dispensing outlet 614 to deliver hydrogel and/or a medicament to channel 612.

The kinesthetic sensors 740, 750 respectively disposed between the hand sections 238, 248 and the end effectors 610, 620 each have a function of detecting an external force applied to the end effectors 610, 620. Further, by feeding back the force detected by the kinesthetic sensors 740, 750 to the robot control device 900, the robot 100 can more precisely perform the operation. Further, contact between the end effectors 610, 620 and an obstacle can be detected using the force and the moment detected by the kinesthetic sensors 740, 750.

Medicaments

The oral appliance contains one or more medicaments coated or layered on it or impregnated within it at the same or different areas to form a monolithic oral appliance. In various embodiments, some areas of the polymer material of the oral appliance do not contain one or more medicaments, and the polymer material may function to hold or lock a portion of the polymer material in place so that other portions of the polymer material can contact the appropriate target site. Thus, in some embodiments, the polymer material may contain one or more medicaments disposed in or on it throughout the whole polymer material of the oral appliance. In other embodiments, one or more portions of the oral appliance do not contain any medicament disposed in or on it (e.g., the non-porous regions of the oral appliance). The term "medicament" as used herein is generally meant to refer to any substance that alters in part or in toto the physiology of a patient. The term "medicament" may be used interchangeably herein with the terms "medicine", "drug" "therapeutic agent", "therapeutically effective amount", or "active pharmaceutical ingredient". It will be understood that a "medicament formulation" may include more than one therapeutic agent, wherein exemplary combinations of therapeutic agents include a combination of two or more medicaments. The medicament can also include cells, where the device (e.g., oral appliance) can be seeded with the cells, for example, gingival cells or gingival tissue, bone cells, cartilage cells, bone tissue so that the device can repair or replace tissue in the treatment area.

The medicament may be in powder, liquid, solid, solution, or suspension (e.g., gel) form and disposed on or impregnated in the oral appliance. This may occur during manufacture of the oral appliance or it may occur after the oral appliance is made. For example, on the core polymer material of the oral appliance, the medicament may be layered by solution or suspension layering or powder layering techniques. In solution or suspension layering, the medicament and any inactive ingredients (excipients, binders, etc.) are suspended or dissolved in water or an organic solvent. The resulting liquid is sprayed onto the outside of the oral appliance to make the polymer material have the desired potency. Solution or suspension layering may be conducted using a wide variety of process techniques, for example, by fluidized bed, Wurster bottom spray techniques, or the like. When the desired potency has been achieved, the polymer material is dried to the desired residual moisture content. Powdered layering involves the application of a dry powder to the oral appliance. The powder may contain the drug, or may include excipients such as a binder, flow aid, inert filler, and the like. In the powder layering technique, a pharmaceutically acceptable liquid, which may be water, organic solvent, with or without a binder and/or excipient, is applied to the oral appliance while applying the dry powder until the desired potency is achieved. When the desired potency has been achieved, the oral appliance may be dried to the desired moisture content.

In various embodiments, the medicament is in liquid form and is capable of diffusing through and within the oral appliance comprising a polymer material. In various embodiments, the liquid medicament may flow or diffuse from one portion of the oral appliance to another portion. In some embodiments, the liquid medicament may not flow or diffuse within the oral appliance. In some embodiments, the liquid medicament is confined within the regions of the oral appliance corresponding to the treatment area. The liquid medicament is not capable of flowing or diffusing into the non-porous regions of the oral appliance. In some embodiments, the liquid medicament may flow or diffuse into the non-porous regions; however, the medicament cannot easily flow or diffuse out of the non-porous regions.

Examples of medicaments include, but are not limited to, anti-inflammatory agents, anti-infective agents (e.g., antiviral, antibacterial, antifungal agents, etc.), tissue and bone growth factors, pain management medication (e.g., analgesics, anesthetics, etc.) antineoplastic agents, tooth whitening agents, breath fresheners, anticalculus agents, antineoplastic agents, oral dermatologics, selective H-2 antagonists, anticaries agents, nutrients, vitamins, minerals, herbal products, opioids, or mixtures thereof.

In various embodiments, the oral appliance may contain more than one medicament. However, in another embodiment, combination therapy will involve use of a single, safe and effective amount of the medicament. For example, the method may further comprise subsequently administering one or more additional oral appliances, each containing a medicament that is different from the medicament contained in the earlier oral appliance. In this way, a series of customized treatment regimens can be provided to the patient. This provides for a "mix and match" medicament regimen with dose adjustment capability and provides the added advantage of allowing the health professional complete control to administer only those medicaments at the desired strength believed to be appropriate for the disease or condition being treated to a particular individual.

In various embodiments, the oral appliance can contain an antimicrobial agent, an anti-inflammatory agent, an antiseptic agent, a probiotic, an immunologic agent, an astringent agent, or a mixture thereof. In some aspects, the antiseptic agent is chlorhexidine digluconate disposed in a porous material comprising a polymer, for example hydrogel.

The amount of medicament contained within the oral appliance, will vary widely depending on the effective dosage required and rate of release from the polymer material and the length of the desired delivery interval. The dosage administered to the patient can be single or multiple doses and will vary depending upon a variety of factors, including the agent's pharmacokinetic properties, patient conditions and characteristics (sex, age, body weight, health, size, etc.), extent of symptoms, concurrent treatments, frequency of treatment and the effect desired. These factors can readily be determined by those of ordinary skill in the art. In some embodiments, the surface area can be calculated to treat a specific targeted area which corresponds to the surface area of the channel such that the treated area is precisely calculated to a specific individual based on that person's specific geometries and not based on the size or weight of the patient.

In various embodiments, the polymer material of the oral appliance is designed to release the medicament as a bolus dose of the medicament, a single dose of the medicament, or multiple doses of the medicament all preloaded with a specific dosage at the manufacturing facility.

In some embodiments, the medicament described herein is in the oral appliance in an amount of from about 0.01, 0.02, 0.03, 0.04, 0.05, 0.06, 0.07, 0.08, 0.09, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, to about 50% by weight of the oral appliance.

The oral appliance may comprise a safe and effective amount of one or more whitening agents such as bleaching agents or abrasive agents. Generally, the level of the bleaching agent is dependent on the available oxygen or chlorine respectively that the molecule is configured for providing to bleach the stain. The bleaching agent may be present at levels from about 0.1% to about 20%, in another embodiment from about 0.5% to about 9% and in another embodiment from about 3% to about 8%, and in yet another embodiment from about 4% to about 6%, by weight of the bleaching agent composition.

In some embodiments, the medicament can be disposed anywhere in or on the interior or exterior surface of the oral appliance adjacent to the gum and/or other soft tissue areas of the oral cavity including the buccal, lingual, palatal, mesial, distal, occlusal surfaces of one or more teeth. Some portions of teeth that do not require the medicament are sealed with the non-porous material which can be a coating, cross-linked with porosity reducing agent or comprise non-porous material such that the medicament cannot penetrate said portions. In some embodiments, the medicament may be disposed in or may enter the non-porous region. However, the medicament disposed in the non-porous region will not release the medicament or will release the medicament at a reduced rate.

In some embodiments, the medicament may enter the non-porous regions, but the medicament will release slowly from these regions. For example, the medicament can be disposed at discrete non-porous regions adjacent to the treatment area or uniformly disposed throughout the device. In this example, the medicament will not be released to other regions that do not correspond with the treatment area.

Methods of Making the Oral Appliance

The oral appliance is custom made to fit a specific patient. The custom-made oral appliance may be prepared by a health care professional including, but not limited to a dentist, oral surgeon, medical doctor, technician or manufacturer. The oral appliance can be made from an impression mold, or by using an analog or digital image capturing device. The oral appliance disclosed herein is not a boil and bite prefabricated device or a stock tray which can be manipulated by the consumer himself/herself with fingers to shape it against the teeth and gums. The oral appliance disclosed herein is custom fit, disposable, and monolithic such that it is pre-loaded with medicament in or on at least a portion of the interior and/or exterior surfaces of the appliance and can deliver medicaments. The medicament can be pre-loaded as part of the oral appliance or infused into the polymer of the oral appliance after the oral appliance is made.

The processes described herein can produce oral appliances with a variety of different properties. Hence in some embodiments the oral appliances are rigid; in other embodiments the products are flexible or resilient. In some embodiments, the oral appliances are a solid; in other embodiments, the oral appliances are a gel such as a hydrogel or have layers of such. In some embodiments, the oral appliances have a shape memory (that is, return substantially to a previous shape after being deformed, so long as they are not deformed to the point of structural failure).

Computer Implemented System

In various embodiments, the present disclosure provides a computer implemented method of making an oral appliance. The method comprises creating a digital record of a patient's oral cavity, the Base Image (BI), by obtaining a digital image of at least a portion of the teeth, and/or soft tissue of the oral cavity by using an imaging device. The Base Image is additively overlaid to create a first digital image, Dig1. Subsequently, a second digital image, Dig2, comprising at least a portion of the teeth and/or soft tissue of the oral cavity in need of treatment is subtractively generated. Thereafter, the first digital image, Dig1, and the second digital image, Dig2, are combined to form a third digital image, Dig3, of the oral cavity treatment area and the third digital image is then stored in the computer and used for manufacture. In other embodiments, the oral appliance is made by traditional vacuum based methods using thermoplastic materials which are softened with heat and then vacuum formed over a model of the patient's mouth including all areas of interest to be treated as described in U.S. Pat. No. 6,386,869 to Zegarelli, P. J.

In some embodiments, there is a computer implemented method of producing an oral appliance pre-loaded with at least one medicament using a computer, comprising: using the Base Image of the digital image of the patient's mouth, generating first digital data representing an overlay of at least a portion of the teeth and/or soft tissues areas of the oral cavity of a patient, generating second digital data by performing a digital segmentation of at least a portion of the teeth and/or soft tissues areas of the oral cavity to determine discrete regions of the oral cavity in need of treatment, combining the first digital data and the second digital data to form the third digital data from which the oral appliance can be produced, wherein the third digital data comprises positions for at least one medicament to be placed at the discrete regions in the oral cavity in need of treatment.

In other embodiments, a computer-implemented method is provided for creating a treatment plan for delivering a medicament to at least a portion of the teeth and/or soft tissue areas inside the oral cavity. The computer-implemented method comprises generating a first digital data, Dig1, representing at least a portion of the teeth and/or soft tissues areas of the oral cavity of a patient from the Base Image. Subsequently, a second digital data, Dig2, is generated by performing via the computer a digital segmentation of at least a portion of the teeth and/or soft tissues areas of the oral cavity comprising discrete regions of the oral cavity in need of treatment. The first digital data, Dig1, and the second digital data, Dig2, are then combined via computer to form the third digital data, Dig3, from which the oral appliance can be produced, wherein the oral appliance has at least one medicament positioned at the discrete regions requiring treatment in the oral cavity.

In various embodiments, the X, Y, Z coordinates of the hydrogel channel and/or reservoir are created (Dig2) digitally in such a way that a robot can "read" the coordinate datapoints in order to create a precise guideline (Dig2a) for the dispensing robotic arm to precisely dispense the hydrogel strip, bead or reservoir onto or into the oral appliance according to the Dig2 mapping system. In some embodiments, Dig2a is a digital coordinate imprint onto Dig3 to specifically guide the robot in dispensing the medicament into the Dig2 portion of Dig3. By using the series of XYZ coordinate guideline (Dig2a), the robotic arm can dispense the hydrogel bead along the proper line(s) or point(s) and does so in the prescribed widths, lengths and depths in a smooth way so that the medicament is distributed evenly and precisely. Each tooth and/or anatomical part of the oral cavity can be defined by from about 1 to about 50 points, each point defined by at least Cartesian coordinates X, Y and Z that are sent to the processor to generate a guideline (Dig2a). For example, in one embodiment, each tooth can be defined by at least 10 Cartesian X, Y, Z coordinates or approximately at least about 160 per guideline. Moreover, by using the zero-point marker reference, the robotic dispensing arm can then orient where the guideline is in three dimensions to calibrate exactly where to begin to dispense hydrogel or other porous material. The guideline Dig2a can be a real line or another marker on the oral appliance itself utilizing a modification of the image of the oral appliance or may only be a digital representation of a line. Thus, guideline Dig2a can be a line or a series of points along the anatomic geometries of the mouth, such as points on the teeth, the gum line or other place markers.

In other embodiments, a computer-based system further comprises creating a virtual 3D image of the oral appliance indicating the discrete regions requiring treatment in the oral cavity; displaying on a display the virtual 3D image and performing interactive treatment plans including the selection of the at least one medicament. Imaging devices utilized to generate the various digital data sets include, without limitations, a digital camera, X-ray device, hand-held 3-D scanner, laser scanner, computerized tomography (CT) scanner, magnetic resonance imaging (MRI) scanner, coordinate measuring machine, destructive scanner or ultrasound scanner, generating first digital data, Dig1, representing at least a portion of the teeth and/or soft tissues areas of the oral cavity of a patient based on an imaging device image (Base Image), generating second digital data, Dig2, by performing via the computer a digital segmentation of at least a portion of the teeth and/or soft tissues areas of the oral cavity comprising discrete regions of the oral cavity in need of treatment, combining via the computer the first digital data, Dig1, and the second digital data, Dig2, to form the third digital data, Dig3, from which the oral appliance can be produced having at least one medicament positioned at the discrete regions requiring treatment in the oral cavity. In some aspects, obtaining the baseline digital image of at least a portion of the patient's teeth, and/or soft tissue of the patient's oral cavity or Dig1 further comprises digitally storing a permanent record of the topography of least a portion of the patient's teeth, and/or soft tissue of the patient's oral cavity for future iterations of oral appliances.

In other embodiments, the three-dimensional representation of the third digital data, Dig3, is stored in a format suitable for use by a manufacturer to produce the oral appliance pre-loaded with at least one medicament at areas targeted for treatment. A stereolithography apparatus comprising at least two print heads can be used to manufacture the oral appliances described in this disclosure. As discussed above, the first print head can be configured to deliver a first chemical composition according to the first digital data, Dig1, and the second print head can be configured to deliver a second chemical composition according to the second digital data, Dig2. The two combined merge and represent the image of the third digital data, Dig3. At least one of the chemical compositions includes a medicament while the other can be a polymer gel, hydrogel, brush polymer, another medicament or combinations thereof.

Figure 8:
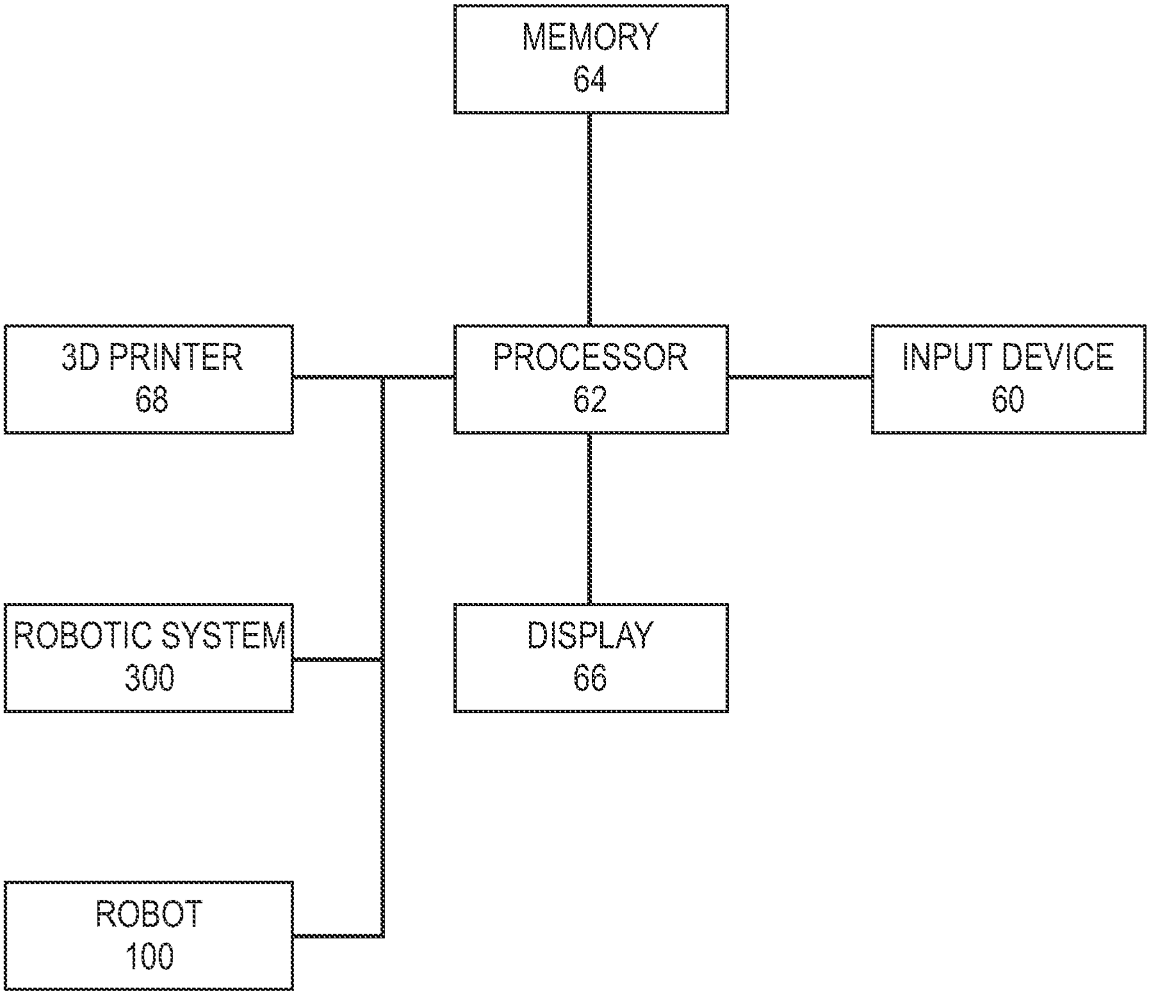
FIG. 8 is a block diagram of one embodiment of components to a computer-implemented system for producing an oral appliance by 3D printing or additive manufacturing or by a robotic system or a robot.

FIG. 8 illustrates an embodiment of the computer-implemented system for producing an oral appliance. An input device or scanner 60 is used to scan the oral cavity of and thus generate a digital record of the patient's mouth, a Base Image (BI). The scanner can be an MRI scanner, a CT scanner, a PET scanner, a digital scanner, an X-Ray machine, or an intra-oral scanner, for example. In various embodiments, scanner 60 can scan the patient's teeth, soft tissue, or both to obtain a digital data set of the teeth and/or soft tissue areas inside the mouth from which is generated the base image. The digital data can be stored in a database, such as for example, a computer that has a processor or CPU 62, which sends the digital data to its memory 64 and/or can display it in a virtual 3D image display 66 of processor 62. In some aspects, CPU 62 can be included in robotic dispensing system 300 and is in communication with first robotic arm 302 and second robotic arm 350. In other aspects, CPU 62 can be included in robot 100 as was discussed above. The database and/or processor can comprise an input device (e.g., keyboard, touch screen, voice activation, etc.) to allow a user to enter, display, edit, and/or transmit one or more images from Dig1, Dig2, Dig2a and Dig3. The processor 62 comprises logic to execute one or more instructions to carry instructions of the computer system (e.g., transmit instructions to the 3D printer and/or the robotic system). The logic for executing instructions may be encoded in one or more tangible media for execution by the processor 62. For example, the processor 62 may execute codes stored in a computer-readable medium such as memory 64. The computer-readable medium may be, for example, electronic (e.g., RAM (random access memory), ROM (read-only memory), EPROM (erasable programmable read-only memory)), magnetic, optical (e.g., CD (compact disc), DVD (digital video disc)), electromagnetic, semiconductor technology, or any other suitable medium. Based on memory 64, processor 62 can generate Dig2, Dig2a and Dig3 and thereafter send a 3D image to the 3D printer 68 of a stereolithography apparatus or robotic dispensing system 300 or robot 100. Based on memory 64, processor 62 can receive image files from sensors 328 and 370 of robotic dispensing system 300 or sensors 250, 270, 740 and 750 of robot 100.

In various embodiments, an authorized user can input, edit data and approve or prescribe a treatment plan based on the virtual 3D images displayed at the user interface of the computer processor 62 and/or another treating computer networked with computer processor 62. Although the components of the system of FIG. 8 are shown as separate, they may combine in one or more computer systems. Indeed, they may be one or more hardware, software, or hybrid components residing in (or distributed among) one or more local or remote computer systems. It also should be readily apparent that the components of the system as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed. Indeed, even a single general-purpose computer (or other processor-controlled device) executing a program stored on an article of manufacture (e.g., recording medium or other memory units) to produce the functionality referred to herein may be utilized to implement the illustrated embodiments. It also will be understood that the a plurality of computers or servers can be used to allow the system to be a network based system having a plurality of computers linked to each other over the network or Internet or the plurality of computers can be connected to each other to transmit, edit, and receive data via cloud computers.

The computer (e.g., memory, processor, storage component, etc.) may be accessed by authorized users. Authorized users may include at least one dentist or dental specialist, dental hygienist, oral surgeon, physician, surgeon, nurse, patient, and/or health care provider, manufacturer, etc.).

The user can interface with the computer via a user interface that may include one or more display devices (e.g., CRT, LCD, or other known displays) or other output devices (e.g., printer, etc.), and one or more input devices (e.g., keyboard, mouse, stylus, touch screen interface, or other known input mechanisms) for facilitating interaction of a user with the system via user interface. The user interface may be directly coupled to database or directly coupled to a network server system via the Internet or cloud computing. In accordance with one embodiment, one or more user interfaces are provided as part of (or in conjunction with) the illustrated systems to permit users to interact with the systems.

The user interface device may be implemented as a graphical user interface (GUI) containing a display or the like, or may be a link to other user input/output devices known in the art. Individual ones of a plurality of devices (e.g., network/stand-alone computers, personal digital assistants (PDAs), WebTV (or other Internet-only) terminals, set-top boxes, cellular/phones, screen phones, pagers, blackberry, smart phones, iPhone, iPad, table, peer/non-peer technologies, kiosks, or other known (wired or wireless) communication devices, etc.) may similarly be used to execute one or more computer programs (e.g., universal Internet browser programs, dedicated interface programs, etc.) to allow users to interface with the systems in the manner described. Database hardware and software can be developed for access by users through personal computers, mainframes, and other processor-based devices. Users may access and data stored locally on hard drives, CD-ROMs, stored on network storage devices through a local area network, or stored on remote database systems through one or more disparate network paths (e.g., the Internet).

The database can be stored in storage devices or systems (e.g., Random Access Memory (RAM), Read Only Memory (ROM), hard disk drive (HDD), floppy drive, zip drive, compact disk-ROM, DVD, bubble memory, flash drive, redundant array of independent disks (RAID), network accessible storage (NAS) systems, storage area network (SAN) systems, etc.), CAS (content addressed storage) may also be one or more memory devices embedded within a CPU, or shared with one or more of the other components, and may be deployed locally or remotely relative to one or more components interacting with the memory or one or more modules. The database may include a data storage device, a collection component for collecting information from users or other computers into centralized database, a tracking component for tracking information received and entered, a search component to search information in the database or other databases, a receiving component to receive a specific query from a user interface, and an accessing component to access centralized database. A receiving component is programmed for receiving a specific query from one of a plurality of users. The database may also include a processing component for searching and processing received queries against data storage device containing a variety of information collected by the collection device.

The disclosed system may, in some embodiments, be a computer network-based system. The computer network may take any wired/wireless form of known connective technology (e.g., corporate or individual LAN, enterprise WAN, intranet, Internet, Virtual Private Network (VPN), combinations of network systems, etc.) to allow a server to provide local/remote information and control data to/from other locations (e.g., other remote database servers, remote databases, network servers/user interfaces, etc.). In accordance with one embodiment, a network server may be serving one or more users over a collection of remote and disparate networks (e.g., Internet, intranet, VPN, cable, special high-speed ISDN lines, etc.). The network may comprise one or more interfaces (e.g., cards, adapters, ports) for receiving data, transmitting data to other network devices, and forwarding received data to internal components of the system (e.g., 3D printers, printer heads, etc.).

In accordance with one embodiment of the present application, the data may be downloaded in one or more textual/graphical formats (e.g., RTF, PDF, TIFF, JPEG, STL, XML, XDFL, TXT etc.), or set for alternative delivery to one or more specified locations (e.g., via e-mail, fax, regular mail, courier, etc.) in any desired format (e.g., print, storage on electronic media and/or computer readable storage media such as CD-ROM, etc.). The user may view the search results and underlying documents at the user interface, which allows viewing of one or more documents on the same display.

In various embodiments, the computer software can create a 2D or 3D digital image of the patient's oral cavity to allow the treatment provider to review and discuss the proposed treatment with the patient. In another embodiment, the software can process the scanned data and provide the user/operator with useful data including tooth measurements (e.g. arch width, arch length, tooth size, angulations, sulcus size, etc.) to assist the user in fine-tuning the treatment plan. The computer can then provide the operator with options in staging the treatment plan from one stage to another stage, or it can completely generate all the stages ranging from the initial to the final desired stage. The staging can be done automatically.

Figure 9:
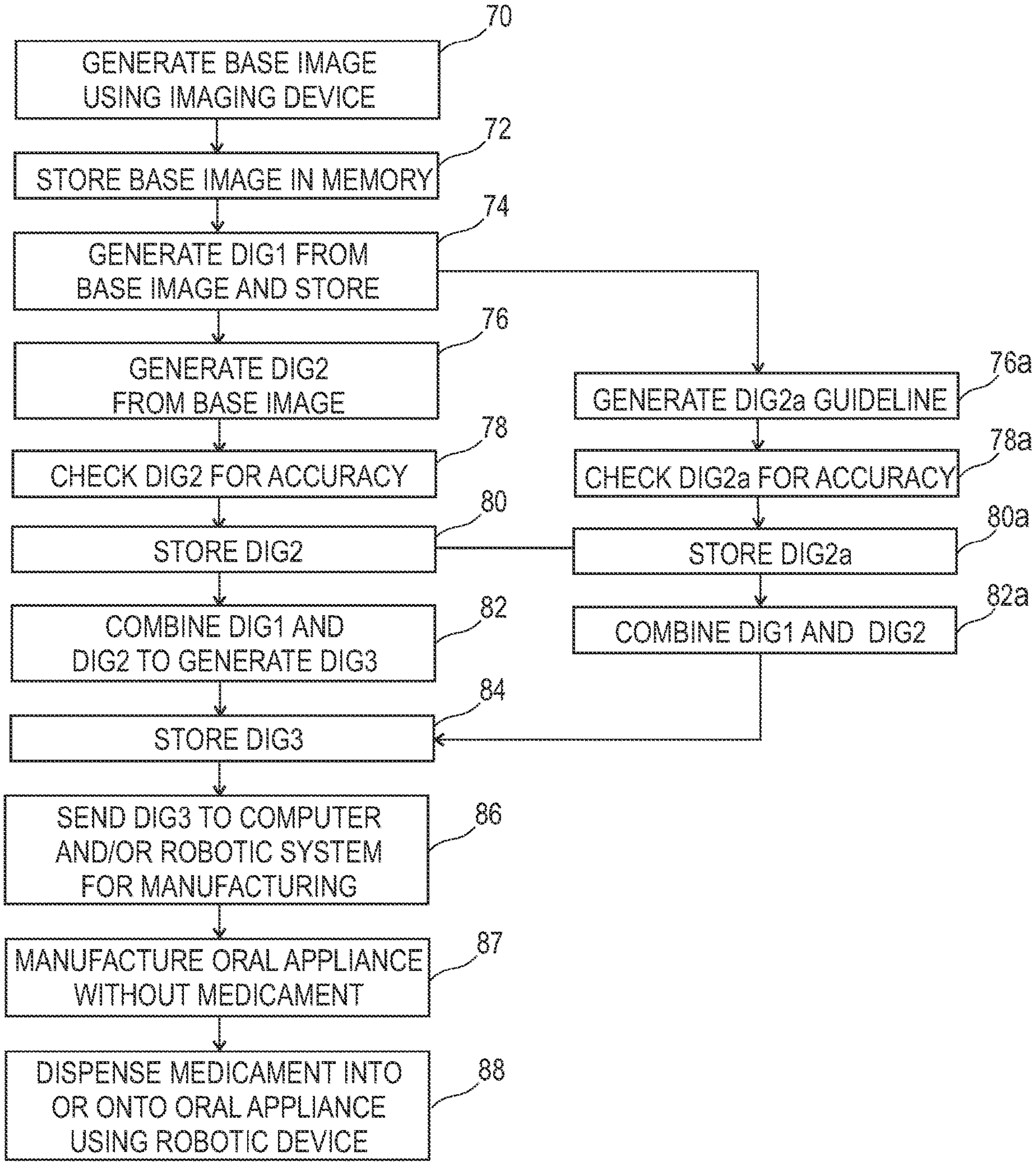
FIG. 9 is a flow chart illustrating one embodiment of the computer-implemented system and steps that the computer performs to produce the oral appliance, which is then loaded with medicament by a robotic system or a robot.

FIG. 9 is a flow chart illustrating the logic steps followed by processor 62. The first step 70 comprises generating a Base Image (BI) of at least a portion of the teeth and/or soft tissues by using an imaging device. In step 72, the BI is stored in the memory of the processor. In step 74, a first data set (Dig1) is generated by the computer additively layering over the BI of at least a portion of the teeth and/or soft tissues. The Dig1 is stored.

In step 76, a second data set (Dig2) is generated by digitally segmenting at least a portion of the teeth and/or soft tissues from the Base Image. Thereafter, in step 78, the processor can decide if all discrete regions of the oral cavity in need of treatment have been identified or if they have not been, then the digital segmentation step will occur again. Dig2 will also be checked for accuracy. In some embodiments, in step 76*a*, the second set of data is defined by a guideline Dig2a. Dig2a is generated by defining each tooth and/or anatomical part of the oral cavity from about 1 to about 50 points, each point defined by at least Cartesian coordinates X, Y and Z and which are sent to processor 62. In step 78*a*, Dig2a is checked for accuracy and then stored in step 80*a*. In other aspects, the second digital image (Dig2) of the patient's oral appliance can be combined with the digital image of the guideline (Dig2a) to facilitate dispensing of the porous material at discrete regions of the oral appliance.

If all the desired discrete regions have been identified, then in step 80, the processor stores the data, which includes the discrete regions in need of treatment as a separate set corresponding to Dig2. The first and second data sets are combined in step 82 to generate a third data set corresponding to Dig3. In some aspects, the third digital data (Dig3) is formed by one of (i) subtracting the second digital data (Dig2) and the digital image of the guideline (Dig2a) from the first digital data (Dig1) or (ii) adding the second digital data (Dig2) and the digital image of the guideline (Dig2a) to the first digital data (Dig1) as illustrated in step 82*a*. The third data set Dig3 is stored in step 84 and then sent to a 3D printer in step 86, or for manufacturing of the oral appliance without medicament in step 87 or with medicament in step 88, wherein steps 86, 87 and 88 are accomplished with the help of a robotic system or robot. In yet other embodiments, the software manipulation accomplished by the robotic system(s) and/or robot(s) described in this application can be accomplished by using artificial intelligence. For example, in one embodiment, Dig2a can be created by artificial intelligence. In yet another embodiment, the Dig1 image is modified to create the handle in a specific location on the oral appliance either incorporating a zero-point marker on the handle or designating a zero-point marker on another aspect of the oral appliance. Still another embodiment, is to modify the Dig2 image and have the handle and/or the zero-point marker created digitally and have that image additively attached to generate the final Dig3 image. In other embodiments, Dig2a is a digital coordinate imprint onto Dig3 to specifically guide the robot in dispensing the medicament into the Dig2 portion of Dig3.

While particular embodiments of the present disclosure have been shown and described, it will be appreciated by those skilled in the art that, based upon the teachings herein, changes and modifications may be made without departing from this disclosure and its broader aspects and, therefore, the appended claims are to encompass within their scope all such changes and modifications as are within the true spirit and scope of this disclosure. The true spirit and scope is considered to encompass devices and processes, unless specifically limited to distinguish from known subject matter, which provide equivalent functions as required for interaction with other elements of the claims and the scope is not considered limited to devices and functions currently in existence where future developments may supplant usage of currently available devices and processes yet provide the functioning required for interaction with other claim elements.

The invention claimed is:

1. A method of making an oral appliance for delivering a medicament to an oral cavity, the method comprising providing an oral appliance having an exterior and an interior, the interior of the oral appliance configured to contour at least a portion of teeth and/or soft tissue areas of the oral cavity; providing a robotic dispensing device having an outlet configured to dispense medicament at discrete regions of the interior, the exterior or both the interior and the exterior of the oral appliance; and dispensing the medicament from the outlet of the robotic dispensing device to discrete regions of the interior, the exterior or both the interior and the exterior of the oral appliance for delivering the medicament to the oral cavity, wherein the oral appliance comprises a projection and/or recess, and the robotic dispensing device comprises a robotic arm comprising a wrist and a gripper connected to the wrist such that the gripper is configured to grip the projection and/or recess of the oral appliance and the wrist is configured to laterally move the gripper allowing the medicament to be dispensed on the oral appliance, wherein the oral appliance further comprises a reference marker configured to register the oral appliance's spatial position and orientation relative to the robotic dispensing device, wherein the robotic dispensing device further comprises a sensor configured to detect the reference marker on the oral appliance, wherein the method comprises providing a guideline comprising X-Y-Z cartesian coordinates corresponding to the detected reference marker, and wherein the projection and/or recess comprises a handle, a gripping surface, or a combination thereof configured to mate with the robotic arm such that the robotic arm repositions and reorients the oral appliance and the outlet following the guideline to dispense the medicament at the X-Y-Z cartesian coordinates of the oral appliance corresponding to the oral cavity for delivering the medicament thereto.

2. The method of claim 1, wherein the robotic arm is coupled to the outlet to dispense a precise dose of the medicament at the discrete regions of the oral appliance.

3. The method of claim 2, wherein the discrete regions are adjacent to a treatment area and the medicament is configured to contact the treatment area.

4. The method of claim 1, wherein the oral appliance comprises an actual or virtual channel configured to receive the medicament from the outlet of the robotic dispensing device.

5. The method of claim 4, wherein the channel is continuous in the interior of the oral appliance and extends along a gum line perimeter.

6. The method of claim 1, wherein the projection and/or recess is removable from the oral appliance.

7. The method of claim 1, wherein the handle, the gripping surface, or combination thereof is configured to remain on the oral appliance to assist a patient during insertion and removal of the oral appliance.

8. The method of claim 4, wherein the oral appliance comprises a barrier for providing a seal between the channel and at least a portion of the teeth and/or the soft tissue areas of the oral cavity.

9. The method of claim 1, wherein the outlet comprises a dispensing tip oriented at about 90 degrees from a vertical axis for maximizing gravitational flow of the medicament into the oral appliance when also lessening a dispensing pressure by the robotic dispensing device.

10. The method of claim 1, wherein before the medicament is dispensed, the oral appliance is made by thermoforming, additive manufacturing, or injection molding.

* * * * *